(12) United States Patent
Frohberg

(10) Patent No.: US 6,794,558 B1
(45) Date of Patent: Sep. 21, 2004

(54) NUCLEIC ACID MODULE CODING FOR αGLUCOSIDASE, PLANTS THAT SYNTHESIZE MODIFIED STARCH, METHODS FOR THE PRODUCTION AND USE OF SAID PLANTS, AND MODIFIED STARCH

(75) Inventor: Claus Frohberg, Berlin (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/744,926

(22) PCT Filed: Jul. 30, 1999

(86) PCT No.: PCT/EP99/05536

§ 371 (c)(1),
(2), (4) Date: Jan. 30, 2001

(87) PCT Pub. No.: WO00/08175

PCT Pub. Date: Feb. 17, 2000

(30) Foreign Application Priority Data

Jul. 31, 1998 (DE) .......................... 198 36 097

(51) Int. Cl.[7] .......................... A01H 5/00; C12N 15/09; C12N 15/63; C12N 15/79; C12N 15/82
(52) U.S. Cl. ...................... 800/284; 800/278; 800/298; 536/23.1; 536/23.2; 536/23.6; 435/419; 435/320.1
(58) Field of Search .............................. 435/320.1, 419, 435/468; 800/278, 284, 298, 317.2; 536/23.1, 23.2, 23.6

(56) References Cited

U.S. PATENT DOCUMENTS 5,763,252 A   6/1998   Skadsen et al.

FOREIGN PATENT DOCUMENTS

| EP | 0 779 363 A2 | | 6/1997 |
|---|---|---|---|
| WO | WO 92/14827 | | 9/1992 |
| WO | WO 94/09144 | | 4/1994 |
| WO | WO 95/07355 | | 3/1995 |
| WO | WO 96/15248 | | 5/1996 |
| WO | WO 97/11188 | | 3/1997 |
| WO | WO 97/16554 | | 5/1997 |
| WO | WO 97/24448 | * | 7/1997 |

OTHER PUBLICATIONS

Sugimoto et al., "Molecular Cloning and Characterization of a cDNA encoding α-glucosidase From Spinach", Plant Molecular Biology, vol. 33, pp. 765–768, 1997.

* cited by examiner

Primary Examiner—David T. Fox
Assistant Examiner—Russell Kallis
(74) Attorney, Agent, or Firm—Frommer Lawrence & Haug LLP

(57) ABSTRACT

The present invention relates to nucleic acid molecules which encode a protein with the activity of a potato α-glucosidase and to processes for the generation of transgenic plant cells and plants which synthesize a modified starch. Moreover, the present invention relates to vectors and host cells comprising the nucleic acid molecules according to the invention, to the plant cells and plants originating from the processes according to the invention, to the starch synthesized by the plant cells and plants according to the invention, and to processes for the production of this starch.

13 Claims, 1 Drawing Sheet

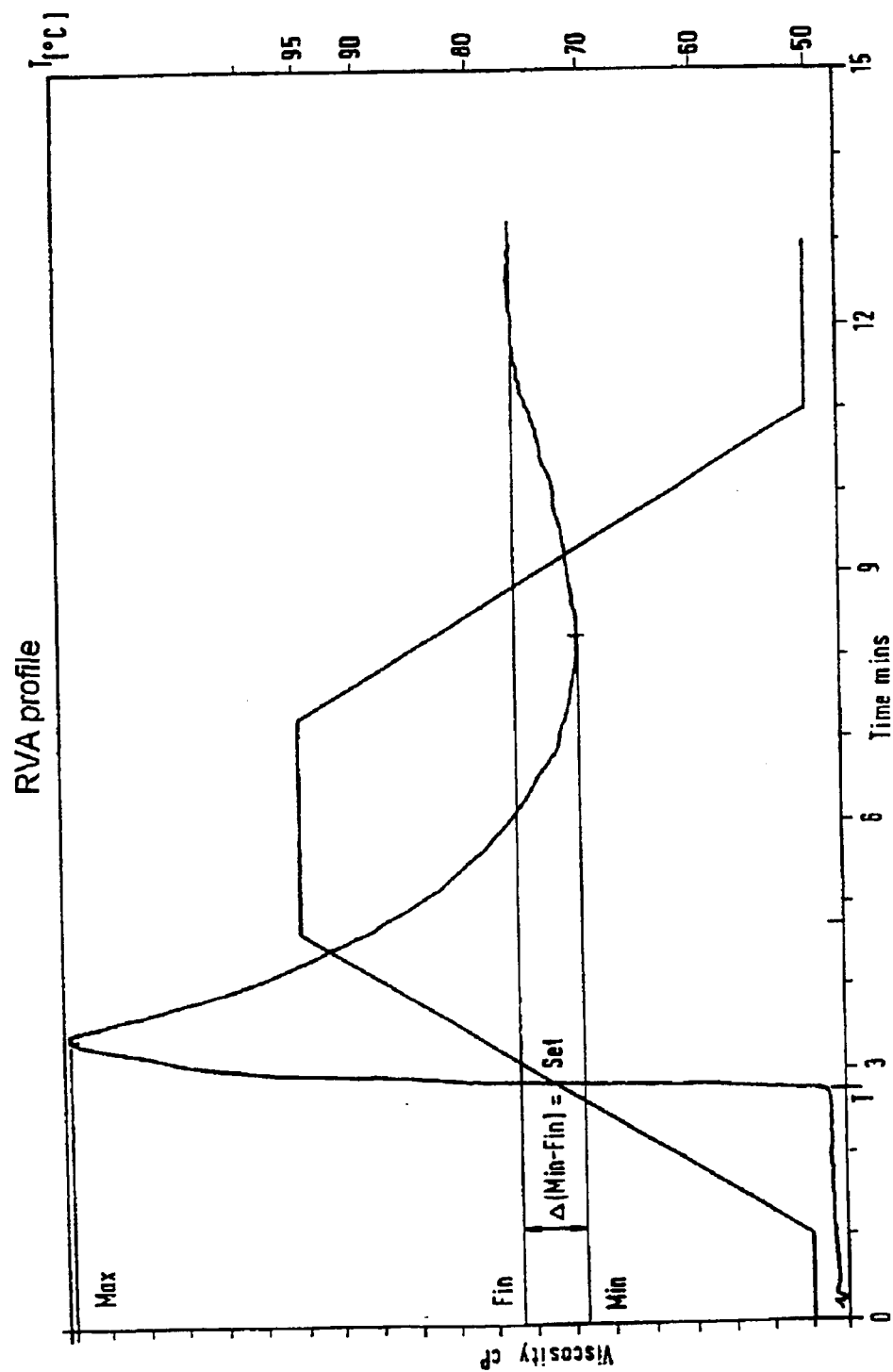

SEQUENCE LISTING

```
<160> NUMBER OF SEQ ID NOS: 2

<210> SEQ ID NO 1
<211> LENGTH: 2272
<212> TYPE: DNA
<213> ORGANISM: Solanum tuberosum
<220> FEATURE:
<221> NAME/KEY: CDS
<222> LOCATION: (135)..(2180)
<223> OTHER INFORMATION: coding sequence of alpha-glucosidase

<400> SEQUENCE: 1
cgaatacgaa taccgacgc taaccatcaa cgatgggaag tgccggaaga aattctccac      60
cgtccaccac cgccgtcgcc gccgtcaacc tccaactcct catcagaaaa ccactcccca     120
attaccctct ctaa ccc aaa ctc aga cct aga gtt cac cct tca caa cac       170
              Pro Lys Leu Arg Pro Arg Val His Pro Ser Gln His
                1               5                   10 cat ccc att cag ctt cac cgt ccg ccg gcg ctc cac cgg gga tac tct       218
His Pro Ile Gln Leu His Arg Pro Pro Ala Leu His Arg Gly Tyr Ser
        15                  20                  25 ttt cga tac ttc gcc gga gtt agt cat ggg gtt ttg ctt ctg agt agc       266
Phe Arg Tyr Phe Ala Gly Val Ser His Gly Val Leu Leu Leu Ser Ser
    30                  35                  40 aat ggc atg gat att gtg tat acg ggt gat agg att agt tac aag gtg       314
Asn Gly Met Asp Ile Val Tyr Thr Gly Asp Arg Ile Ser Tyr Lys Val
45                  50                  55                  60 att gga ggg tta att gat ttg tat ttc ttt gcc gga cct tcg ccg gaa       362
Ile Gly Gly Leu Ile Asp Leu Tyr Phe Phe Ala Gly Pro Ser Pro Glu
                65                  70                  75 atg gtg gtg gat cag tat act cag ctt att ggt cgt cct gct gct atg       410
Met Val Val Asp Gln Tyr Thr Gln Leu Ile Gly Arg Pro Ala Ala Met
            80                  85                  90 cca tat tgg tct ttc gga ttt cac caa tgc cgg tgg ggt tac aag aat       458
Pro Tyr Trp Ser Phe Gly Phe His Gln Cys Arg Trp Gly Tyr Lys Asn
        95                  100                 105 att gat gat gtt gaa ctg gta gtg gat agt tat gca aag tct aga ata       506
Ile Asp Asp Val Glu Leu Val Val Asp Ser Tyr Ala Lys Ser Arg Ile
    110                 115                 120
```

-continued

| | |
|---|---|
| ccg ctg gag gtt atg tgg act gat att gat tac atg gat ggt ttt aag<br>Pro Leu Glu Val Met Trp Thr Asp Ile Asp Tyr Met Asp Gly Phe Lys<br>125                           130                       135                       140 | 554 |
| gac ttc aca ctc gat cca gtt aac ttc cca ctg gag cgg gta att ttt<br>Asp Phe Thr Leu Asp Pro Val Asn Phe Pro Leu Glu Arg Val Ile Phe<br>                  145                       150                       155 | 602 |
| ttt ctc agg aag ctt cat cag aat gat cag aaa tat gta cta ata gta<br>Phe Leu Arg Lys Leu His Gln Asn Asp Gln Lys Tyr Val Leu Ile Val<br>            160                       165                       170 | 650 |
| gat cca gga att agc atc aac aat aca tat gac acc tat agg aga ggc<br>Asp Pro Gly Ile Ser Ile Asn Asn Thr Tyr Asp Thr Tyr Arg Arg Gly<br>               175                       180                      185 | 698 |
| atg gaa gca gat gtc ttc ata aaa cgc gat aat atg ccc tac caa ggg<br>Met Glu Ala Asp Val Phe Ile Lys Arg Asp Asn Met Pro Tyr Gln Gly<br>190                           195                       200 | 746 |
| gtt gtt tgg cca ggg aat gtt tat tat cct gat ttt cta aat cca gct<br>Val Val Trp Pro Gly Asn Val Tyr Tyr Pro Asp Phe Leu Asn Pro Ala<br>205                           210                       215                       220 | 794 |
| act gaa gta ttt tgg aga aat gaa att gag aag ttc cag gat ctc gta<br>Thr Glu Val Phe Trp Arg Asn Glu Ile Glu Lys Phe Gln Asp Leu Val<br>                     225                       230                       235 | 842 |
| cct ttt gat ggc ctg tgg ctt gac atg aat gaa ttg tca aac ttc ata<br>Pro Phe Asp Gly Leu Trp Leu Asp Met Asn Glu Leu Ser Asn Phe Ile<br>            240                       245                       250 | 890 |
| act tcc cct cct aca cca tca tct acc ttt gat gat cct ccc tac aag<br>Thr Ser Pro Pro Thr Pro Ser Ser Thr Phe Asp Asp Pro Pro Tyr Lys<br>               255                       260                      265 | 938 |
| ata aac aac tct ggc gat cac ttg ccc atc aat tat aga aca gtt cca<br>Ile Asn Asn Ser Gly Asp His Leu Pro Ile Asn Tyr Arg Thr Val Pro<br>270                           275                       280 | 986 |
| gcc act tct aca cat ttt ggt gat aca atg gag tat aat gtc cat aac<br>Ala Thr Ser Thr His Phe Gly Asp Thr Met Glu Tyr Asn Val His Asn<br>285                           290                       295                       300 | 1034 |
| ctt tat gga tta ctt gaa tct aga gcc act tat agt gca ttg gtt aat<br>Leu Tyr Gly Leu Leu Glu Ser Arg Ala Thr Tyr Ser Ala Leu Val Asn<br>                     305                       310                       315 | 1082 |
| gtc act ggt aaa agg cca ttc att ctt gta aga tca act ttt ctt ggc<br>Val Thr Gly Lys Arg Pro Phe Ile Leu Val Arg Ser Thr Phe Leu Gly<br>            320                       325                       330 | 1130 |
| tct ggc aga tac acg tca cat tgg act gga gat aat gct gct acc tgg<br>Ser Gly Arg Tyr Thr Ser His Trp Thr Gly Asp Asn Ala Ala Thr Trp<br>               335                       340                      345 | 1178 |
| aac gat ttg gca tac tcc att cct act atc ttg agc ttt gga ttg ttt<br>Asn Asp Leu Ala Tyr Ser Ile Pro Thr Ile Leu Ser Phe Gly Leu Phe<br>350                           355                       360 | 1226 |
| gga att cca atg gtt gga gct gat ata tgt ggt ttt tca agt aac act<br>Gly Ile Pro Met Val Gly Ala Asp Ile Cys Gly Phe Ser Ser Asn Thr<br>365                           370                       375                       380 | 1274 |
| act gaa gag ctt tgc cgc cgc tgg att cag ctt gga gca ttc tat cca<br>Thr Glu Glu Leu Cys Arg Arg Trp Ile Gln Leu Gly Ala Phe Tyr Pro<br>                    385                       390                       395 | 1322 |
| ttt gca aga gac cac tct gct aag gac aca acc ccc caa gag ctc tat<br>Phe Ala Arg Asp His Ser Ala Lys Asp Thr Thr Pro Gln Glu Leu Tyr<br>               400                       405                       410 | 1370 |
| agt tgg gat tca gtt gct gca gca gcc aag aaa gtc ctt ggg ctc cga<br>Ser Trp Asp Ser Val Ala Ala Ala Ala Lys Lys Val Leu Gly Leu Arg<br>               415                       420                       425 | 1418 |
| tat cag tta ctt cca tac ttt tat atg ctt atg tac gag gca cat ata<br>Tyr Gln Leu Leu Pro Tyr Phe Tyr Met Leu Met Tyr Glu Ala His Ile | 1466 |

```
                430             435             440
aaa ggg act ccc att gca cga ccc ctc ttc ttc tct ttc cct caa gat    1514
Lys Gly Thr Pro Ile Ala Arg Pro Leu Phe Phe Ser Phe Pro Gln Asp
445             450             455             460 gcc aag aca ttt gat atc agc aca cag ttc ctt ctc ggt aaa ggt gtc    1562
Ala Lys Thr Phe Asp Ile Ser Thr Gln Phe Leu Leu Gly Lys Gly Val
                465             470             475 atg atc tca cct ata ctt aag caa gga gca acc tct gtt gat gca tat    1610
Met Ile Ser Pro Ile Leu Lys Gln Gly Ala Thr Ser Val Asp Ala Tyr
            480             485             490 ttc cct gct gga aac tgg ttt gac ctc ttc aat tac tct cgc tct gtg    1658
Phe Pro Ala Gly Asn Trp Phe Asp Leu Phe Asn Tyr Ser Arg Ser Val
        495             500             505 agt ttg aat caa gga aca tat atg aca ctt gac gca cca cca gat cat    1706
Ser Leu Asn Gln Gly Thr Tyr Met Thr Leu Asp Ala Pro Pro Asp His
    510             515             520 ata aat gta cat gtt cgt gaa ggg aac ata ttg gtc atg caa ggg gaa    1754
Ile Asn Val His Val Arg Glu Gly Asn Ile Leu Val Met Gln Gly Glu
525             530             535             540 gca atg aca aca caa gct gct cag agg act gca ttc aaa ctc ctt gtc    1802
Ala Met Thr Thr Gln Ala Ala Gln Arg Thr Ala Phe Lys Leu Leu Val
                545             550             555 gtg ctg agc agc agc aaa aac agc aca gga gaa cta ttt gtg gac gat    1850
Val Leu Ser Ser Ser Lys Asn Ser Thr Gly Glu Leu Phe Val Asp Asp
            560             565             570 gac gat gag gtg cag atg gga aga gag gga ggg agg tgg acg cta gtt    1898
Asp Asp Glu Val Gln Met Gly Arg Glu Gly Gly Arg Trp Thr Leu Val
        575             580             585 aag ttt aac agc aat atc att ggc aat aaa att gtg gtt aaa tca gag    1946
Lys Phe Asn Ser Asn Ile Ile Gly Asn Lys Ile Val Val Lys Ser Glu
    590             595             600 gtt gtg aat gga cga tat gcg ctg gat caa gga ttg gtc ctt gaa aag    1994
Val Val Asn Gly Arg Tyr Ala Leu Asp Gln Gly Leu Val Leu Glu Lys
605             610             615             620 gtg aca tta ttg gga ttt gaa aat gtg aga gga ttg aag agc tat gag    2042
Val Thr Leu Leu Gly Phe Glu Asn Val Arg Gly Leu Lys Ser Tyr Glu
                625             630             635 ctt gtt gga tca cac cag caa ggg aac aca aca atg aag gaa agt ctt    2090
Leu Val Gly Ser His Gln Gln Gly Asn Thr Thr Met Lys Glu Ser Leu
            640             645             650 aag cag agt gga cag ttt gtt act atg gaa atc tca ggg atg tca ata    2138
Lys Gln Ser Gly Gln Phe Val Thr Met Glu Ile Ser Gly Met Ser Ile
        655             660             665 ttg ata ggg aaa gag ttc aaa ttg gag cta tac atc att act            2180
Leu Ile Gly Lys Glu Phe Lys Leu Glu Leu Tyr Ile Ile Thr
    670             675             680 taacaaatga attaagttat atacgcttgt tgtatgaaat tttctttcat ttatcaatgc  2240
agtttaattt atgataaaaa aaaaaaaaa aa                                 2272

<210> SEQ ID NO 2
<211> LENGTH: 682
<212> TYPE: PRT
<213> ORGANISM: Solanum tuberosum

<400> SEQUENCE: 2

Pro Lys Leu Arg Pro Arg Val His Pro Ser Gln His Pro Ile Gln
1               5                   10                  15

Leu His Arg Pro Pro Ala Leu His Arg Gly Tyr Ser Phe Arg Tyr Phe
                20                  25                  30
```

```
Ala Gly Val Ser His Gly Val Leu Leu Ser Ser Asn Gly Met Asp
         35                  40                  45

Ile Val Tyr Thr Gly Asp Arg Ile Ser Tyr Lys Val Ile Gly Gly Leu
50                  55                  60

Ile Asp Leu Tyr Phe Phe Ala Gly Pro Ser Pro Glu Met Val Val Asp
65                  70                  75                  80

Gln Tyr Thr Gln Leu Ile Gly Arg Pro Ala Met Pro Tyr Trp Ser
                 85                  90                  95

Phe Gly Phe His Gln Cys Arg Trp Gly Tyr Lys Asn Ile Asp Asp Val
                100                 105                 110

Glu Leu Val Val Asp Ser Tyr Ala Lys Ser Arg Ile Pro Leu Glu Val
             115                 120                 125

Met Trp Thr Asp Ile Asp Tyr Met Asp Gly Phe Lys Asp Phe Thr Leu
         130                 135                 140

Asp Pro Val Asn Phe Pro Leu Glu Arg Val Ile Phe Phe Leu Arg Lys
145                 150                 155                 160

Leu His Gln Asn Asp Gln Lys Tyr Val Leu Ile Val Asp Pro Gly Ile
                 165                 170                 175

Ser Ile Asn Asn Thr Tyr Asp Thr Tyr Arg Arg Gly Met Glu Ala Asp
                 180                 185                 190

Val Phe Ile Lys Arg Asp Asn Met Pro Tyr Gln Gly Val Val Trp Pro
             195                 200                 205

Gly Asn Val Tyr Tyr Pro Asp Phe Leu Asn Pro Ala Thr Glu Val Phe
         210                 215                 220

Trp Arg Asn Glu Ile Glu Lys Phe Gln Asp Leu Val Pro Phe Asp Gly
225                 230                 235                 240

Leu Trp Leu Asp Met Asn Glu Leu Ser Asn Phe Ile Thr Ser Pro Pro
                 245                 250                 255

Thr Pro Ser Ser Thr Phe Asp Asp Pro Pro Tyr Lys Ile Asn Asn Ser
             260                 265                 270

Gly Asp His Leu Pro Ile Asn Tyr Arg Thr Val Pro Ala Thr Ser Thr
         275                 280                 285

His Phe Gly Asp Thr Met Glu Tyr Asn Val His Asn Leu Tyr Gly Leu
290                 295                 300

Leu Glu Ser Arg Ala Thr Tyr Ser Ala Leu Val Asn Val Thr Gly Lys
305                 310                 315                 320

Arg Pro Phe Ile Leu Val Arg Ser Thr Phe Leu Gly Ser Gly Arg Tyr
                 325                 330                 335

Thr Ser His Trp Thr Gly Asp Asn Ala Ala Thr Trp Asn Asp Leu Ala
             340                 345                 350

Tyr Ser Ile Pro Thr Ile Leu Ser Phe Gly Leu Phe Gly Ile Pro Met
         355                 360                 365

Val Gly Ala Asp Ile Cys Gly Phe Ser Ser Asn Thr Thr Glu Glu Leu
         370                 375                 380

Cys Arg Arg Trp Ile Gln Leu Gly Ala Phe Tyr Pro Phe Ala Arg Asp
385                 390                 395                 400

His Ser Ala Lys Asp Thr Thr Pro Gln Glu Leu Tyr Ser Trp Asp Ser
                 405                 410                 415

Val Ala Ala Ala Lys Lys Val Leu Gly Leu Arg Tyr Gln Leu Leu
             420                 425                 430

Pro Tyr Phe Tyr Met Leu Met Tyr Glu Ala His Ile Lys Gly Thr Pro
         435                 440                 445
```

```
-continued

Ile Ala Arg Pro Leu Phe Phe Ser Phe Pro Gln Asp Ala Lys Thr Phe
    450                 455                 460
Asp Ile Ser Thr Gln Phe Leu Leu Gly Lys Gly Val Met Ile Ser Pro
465                 470                 475                 480
Ile Leu Lys Gln Gly Ala Thr Ser Val Asp Ala Tyr Phe Pro Ala Gly
                485                 490                 495
Asn Trp Phe Asp Leu Phe Asn Tyr Ser Arg Ser Val Ser Leu Asn Gln
            500                 505                 510
Gly Thr Tyr Met Thr Leu Asp Ala Pro Pro Asp His Ile Asn Val His
        515                 520                 525
Val Arg Glu Gly Asn Ile Leu Val Met Gln Gly Glu Ala Met Thr Thr
    530                 535                 540
Gln Ala Ala Gln Arg Thr Ala Phe Lys Leu Leu Val Val Leu Ser Ser
545                 550                 555                 560
Ser Lys Asn Ser Thr Gly Glu Leu Phe Val Asp Asp Asp Asp Glu Val
                565                 570                 575
Gln Met Gly Arg Glu Gly Gly Arg Trp Thr Leu Val Lys Phe Asn Ser
            580                 585                 590
Asn Ile Ile Gly Asn Lys Ile Val Val Lys Ser Glu Val Val Asn Gly
        595                 600                 605
Arg Tyr Ala Leu Asp Gln Gly Leu Val Leu Glu Lys Val Thr Leu Leu
    610                 615                 620
Gly Phe Glu Asn Val Arg Gly Leu Lys Ser Tyr Glu Leu Val Gly Ser
625                 630                 635                 640
His Gln Gln Gly Asn Thr Thr Met Lys Glu Ser Leu Lys Gln Ser Gly
            645                 650                 655
Gln Phe Val Thr Met Glu Ile Ser Gly Met Ser Ile Leu Ile Gly Lys
            660                 665                 670
Glu Phe Lys Leu Glu Leu Tyr Ile Ile Thr
        675                 680
```

NUCLEIC ACID MODULE CODING FOR αGLUCOSIDASE, PLANTS THAT SYNTHESIZE MODIFIED STARCH, METHODS FOR THE PRODUCTION AND USE OF SAID PLANTS, AND MODIFIED STARCH

The present invention relates to nucleic acid molecules which encode a protein with the activity of a potato α-glucosidase, and to processes for the generation of transgenic plant cells and plants which synthesize a modified starch. Moreover, the present invention relates to vectors and host cells comprising the nucleic acid molecules according to the invention, to the plant cells and plants originating from the processes according to the invention, to the starch synthesized by the plant cells and plants according to the invention, and to processes for the production of this starch.

Taking into consideration the increasing importance attached to plant constituents as renewable raw materials, biotechnology research attempts to adapt plant-based raw materials to the needs of the processing industry. To allow renewable raw materials to be used in as many fields of application as possible, it is therefore necessary to provide a multiplicity of substances.

Besides oils, fats and proteins, polysaccharides constitute important renewable raw materials from plants. Besides cellulose, starch, which is one of the most important storage substances in higher plants, occupies a central position amongst the polysaccharides. Besides maize, rice and wheat, potatoes play an important role, in particular in starch production.

The polysaccharide starch is a polymer of chemically uniform units, the glucose molecules. However, it is a highly complex mixture of different forms of molecules which differ with regard to their degree of polymerization and the occurrence of branchings of the glucose chains. Starch therefore constitutes no uniform raw material. In particular, we differentiate between amylose starch, an essentially unbranched polymer of α-1,4-glycosidically linked glucose molecules, and amylopectin starch, which, in turn, constitutes a complex mixture of differently branched glucose chains. The branchings are generated by the occurrence of additional α-1,6-glycosidic linkages. In typical plants used for starch production such as, for example, maize or potatoes, the starch synthesized consists of approx. 25% amylose starch and approx. 75% amylopectin starch.

The molecular structure of starch, which is determined to a great extent by the degree of branching, the amylose/amylopectin ratio, the average length and distribution of the side chains, and the presence of phosphate groups, is decisive for important functional properties of starch or its aqueous solutions. Examples of functional properties which must be mentioned in this context are solubility, the retrogradation behavior, the film-forming properties, the viscosity—the color stability, the gelatinization properties, and binding and adhesive properties. The starch granule size may also be of importance for various uses. Also, the generation of high-amylose starches is of particular interest for certain applications. Furthermore, a modified starch present in plant cells can advantageously modify the behavior of the plant cell under certain conditions. For example, it is feasible to reduce starch breakdown during the storage of starch-containing organs, such as, for example, seeds or tubers, prior to their further processing, for example for extracting the starch. It is furthermore of interest to prepared modified starches which lead to plant cells or plant organs containing this starch being better suited to processing, for example in the production of foods such as popcorn or cornflakes from maize, or the production of French fries, chips or potato powder from potatoes. Of particular interest in this context is an improvement of the starches with regard to reduced cold sweetening, i.e. a reduced liberation of reducing sugars (in particular glucose) upon prolonged storage at low temperatures. Potatoes especially are frequently stored at temperatures from 4 to 8° C. in order to minimize starch breakdown during storage. The reducing sugars liberated during this process, in particular glucose, result in undesired browning reactions (so-called Maillard reactions) in the production of French fries or crisps.

The starch which can be isolated from plants is frequently adapted to particular industrial purposes with the aid of chemical modifications which, as a rule, require time and money. It seems therefore desirable to find possibilities of generating plants which synthesize starch whose properties already meet the specific demands of the processing industry and thus combine economical and ecological advantages.

One possibility of providing such plants is, in addition to plant breeding measures, the directed genetic modification of the starch metabolism of starch-producing plants by recombinant methods. However, a prerequisite therefor is the identification and characterization of the enzymes which participate in starch synthesis modificaton and starch breakdown (starch metabolism) and the isolation of the corresponding DNA sequences which encode these enzymes.

The biochemical synthetic pathways which lead to the synthesis of starch are essentially known. In plant cells, starch synthesis takes place in the plastids. In photosynthetically active tissues, these plastids are the chloroplasts, in photosynthetically inactive, starch-storing tissue the amyloplasts.

Important enzymes which are involved in starch metabolism are, for example, the branching enzymes, ADP glucose pyrophosphorylases, granule-bound starch synthases, soluble starch synthases, debranching enzymes, disproportioning enzymes, plastid starch phosphorylases, the R1 enzymes (R1 proteins), amylases or glucosidases.

It is an object of the present invention to provide other, or alternative, recombinant approaches for modifying the starch metabolism in starch-synthesizing plants (for example rye, barley, oats, maize, wheat, sorghum and millet, sago, rice, peas, marrowfat peas, cassava, potatoes, tomatoes, oilseed rape, soybeans, hemp, flax, sunflowers, cowpeas, mung beans, beans, bananas or arrowroot or) suitable nucleic acid molecules by means of which plant cells can be transformed, thus allowing the synthesis of modified, advantageous starch species.

Such modified starch species exhibit, for example, modifications regarding their degree of branching, the amylose/amylopectin ratio, the phosphate content, the starch granule size and/or the average length and distribution of the side chains (i.e. side chain structure).

It is a further object of the invention to provide methods which allow the generation of transgenic plants which synthesize a modified starch species.

Surprisingly, transgenic plants which have been transformed with the nucleic acid molecules according to the invention synthesize a starch whose physicochemical properties and/or whose side chain structure is modified in the particular manner so that the abovementioned objects are achieved by providing the use forms specified in the claims.

The invention therefore relates to a nucleic acid molecule encoding a protein with the function of a potato α-glucosidase, selected from the group consisting of a) nucleic acid molecules which encode a protein which encompasses the amino acid sequence stated under SEQ ID NO: 2 or its derivatives or parts, b) nucleic acid molecules which encompass the nucleotide sequence shown under SEQ ID NO: 1 or its derivatives or parts, or a corresponding ribonucleotide sequence;

c) nucleic acid molecules which hybridize with, or are complementary to, preferably which hybridize specifically with, the nucleic acid molecules stated under a) or b), and d) nucleic acid molecules whose nucleotide sequence deviates from the sequence of the nucleic acid molecules stated under a), b) or c) owing to the degeneracy of the genetic code.

Accordingly, the present invention relates to a nucleic acid molecule which encodes an α-glucosidase and which comprises an amino acid sequence of SEQ ID NO: 2 or its derivatives or parts in accordance with the cDNA insert of the plasmid (DSM No. 12347). The abovementioned α-glucosidase according to the invention is involved in the starch metabolism of potatoes and is directly or indirectly involved in starch biosynthesis.

The term "derivative" with regard to the α-glucosidase protein (or its polypeptide, amino acid sequence) of the invention encompasses, for the purposes of the present invention, a polypeptide which is derived from SEQ ID NO: 2 and which comprises at least 163 amino acid residues, preferably at least 227, in particular at least 293 and very especially preferably approximately 309–322 amino acid residues which are selected from the group of the amino acid residues consisting of 18H, 25 R, 34 G, 37 H, 38 G, 39 V, 41 L, 42 L, 44 S, 45 N, 46 G, 47 M, 48 D, 51 Y, 53 G, 55 R, 56 I, 58 Y, 60 V, 61 I, 62 G, 63 G, 65 I, 66 D, 67 L, 68 Y, 70 F, 71 A, 72 G, 75 P, 78 V, 81 Q, 83 T, 86 I, 87 G, 86 R, 89 P, 90 A, 92 M, 93 P, 94 Y, 95 W, 97 F, 98 G, 99 F, 101 Q, 102 C, 103R, 105G, 106 Y, 115 V, 116 V, 119 Y, 120 A, 124 I, 125 P, 126 L, 127 E, 128 V, 129 M, 130 W, 131 T, 132 D, 133 I, 134 D, 135 Y, 136 M, 137 D, 140 K, 141 D, 142 F, 143 T, 144 L, 145 D, 146 P, 147 V, 149 F, 150 P, 157 F, 161 L, 162 H, 164 N, 166 Q, 168 Y, 169 V, 171 I, 173 D, 174 P, 175 G, 176 I, 182 Y, 184 T, 187 R, 188 G, 189 M, 193 V, 194 F 196 K, 197 R, 201 P, 202 Y, 204 G, 206 V, 207 W, 208 P, 209 G, 211 V, 212 Y, 214 P, 215 D, 216 F, 217 L, 219 P, 224 F, 225 W, 228 E, 229 I, 232 F, 237 P, 239 D, 240 G, 242 W, 244 D, 245 M, 246 N, 247 E, 249 S, 250 N, 251 F, 252 I, 254 S, 260 S, 263 D, 265 P, 266 P, 267 Y, 268 K, 269 I, 270 N, 271 N, 272 S, 273 G, 277 P, 278 I, 282 T, 284 P, 286 T, 289 H, 291 G, 295 E, 296 Y, 299 H, 300 N, 301 L, 303 G, 305 L, 306 E, 310 T, 313 A, 322 P, 323 F, 325 L, 327 R, 328 S, 329 T, 330 F, 333 S, 334 G, 336 Y, 337 T, 339 H, 340 W, 341 T, 342 G, 343 D, 344 N, 345 A, 346 A, 348 W, 350 D, 351 L, 353 Y, 354 S, 355 I, 356 P, 359 L, 361 F, 362 G, 363 L, 364 F, 365 G, 367 P, 368 M, 370 G, 371 A, 372 D, 373 I, 374 C, 375 G, 376 F, 380 T, 381 T, 382 E, 383 E, 384 L, 385 C, 387 R, 388 W, 389 I, 390 Q, 391 L, 392 G, 393 A, 394 F, 395 Y, 396 P, 397 F, 399 R, 400 D, 401 H, 402 S, 406 T, 409 Q, 410 E, 411 L, 412 Y, 414 W, 416 S, 417 V, 418 A, 421 A, 424 V, 425 L, 426 G, 427 L, 428 R, 431 L, 432 L, 433 P, 436 Y, 438 L, 439 M, 440 Y, 442 A, 446 G, 448 P, 449 I, 450 A, 451 R, 452 P, 453 L, 455 F, 457 F, 458 P, 460 D, 463 T, 468 I, 469 Q, 470 F, 471 L, 473 G, 477 M, 479 S, 480 P, 482 L, 485 G, 489 V, 491 A, 492 Y, 494 P, 496 G, 497 N, 498 W, 501 L, 504 Y, 508 V, 513 G, 518 L, 521 P, 523 D, 524 H, 526 N, 527 V, 528 H, 531 E, 532 G, 534 I, 537 M, 538 Q, 539 G, 541 A, 543 T, 544 T, 547 A, 550 T, 554 L, 555 L, 556 V, 557 V, 559 S, 566 G, 567 E, 568 L, 569 F, 571 D, 579 G, 583 G, 585 W, 586 T, 588 V, 590 F, 603 S, 605 V, 606 V, 611 A, 620 K, 622 T, 625 G, 635 Y, 658 F, 664 S, 669 L, 671 G, 674 F and 678 L of SEQ ID NO: 2 and which comprises at least approximately 1–69, preferably at least 139, in particular at least 194, more preferably at least 249 and very especially preferably approximately 263–274 amino acid residues which are selected from the group of the amino acid residues consisting of 1 P, 2 K, 3 L, 4 R, 5 P, 6 S, 7 V, 8 H, 9 P, 10 S, 11 Q, 12 H, 13 H, 14 P, 15 I, 16 Q, 17 L, 19 R, 20 P, 21 P, 22 A, 23 L, 24 H, 27 Y, 28 S, 29 F, 30 R, 31 Y, 32 F, 35 V, 36 S, 43 S, 49 I, 50 V, 57 S, 64 L, 84 Q, 91 A, 109 I, 110 D, 112 V, 114 L, 118 S, 122 S, 152 E, 153 R, 154 V, 155 I, 156 F, 158 L, 159 R, 163 Q, 165 D, 172 V, 178 I, 180 N, 183 D, 186 R, 198 D, 199 N, 200 M, 203 Q, 205 V, 210 N, 221 T, 222 E, 223 V, 226 R, 230 E, 231 K, 236 V, 238 F, 243 L, 259 S, 262 F, 275 H, 280 Y, 281 R, 288 T, 293 T, 294 M, 311 Y, 312 S, 316 N, 317 V, 326 V, 331 L, 335 R, 338 S, 360 S, 378 S, 404 K, 408 P, 413 S, 420 A, 422 K, 430 Q, 437 M, 444 I, 445 K, 447 T, 461 A, 464 F, 465 D, 468 T, 478 I, 481 I, 487 T, 510 L, 511 N, 512 Q, 516 M, 536 V, 548 Q, 549 R, 551 A, 553 K, 558 L, 560 S, 561 S, 562 K, 570 V, 573 D, 574 D, 577 Q, 580 R, 581 E, 584 R, 591 N, 592 S, 593 N, 594 I, 595 I, 598 K, 599 I, 601 V, 602 K, 609 R, 612 L, 613 D, 615 G, 616 L, 618 L, 619 E, 623 L, 630 R, 631 G, 632 L, 634 S, 637 L, 638 V, 639 G, 641 H, 642 Q, 643 Q, 644 G, 645 N, 646 T, 647 T, 648 M, 649 K, 650 E, 651 S, 652 L, 653 K, 654 Q, 656 G, 657 Q, 659 V, 660 T, 661 M, 665 M, 668 I, 670 I, 679 Y, 680 I, 681 I, 682 T, 693 H, 700 R, 703 G, 705 H, 706 G, 707 V, 709 L, 710 L, 712 S, 713 N, 714 G, 715 M, 716 D, 718 Y, 720 G, 721 R, 722 I, 724 Y, 726 V, 727 I, 728 G, 729 G, 730 I, 731 D, 732 L, 733 Y, 734 F, 735 A, 736 G, 739 P, 742 V, 743 Q, 745 T, 747 I, 748 G, 749 R, 750 P, 751 A, 753 M, 754 P, 755 Y, 756 W, 757 F, 758 G, 759 F, 761 Q, 762 C, 763 R, 764 G, 765 Y, 768 V, 769 V, 771 Y, 772 A, 775 I, 776 P, 777 L, 778 E, 779 V, 780 M, 781 W, 782 T, 783 D, 784 I, 785 D, 786 Y, 787 M, 788 D, 789 K, 790 D, 791 F, 792 T, 793 L, 794 D, 795 P, 796 V, 798 F, 799 P, 804 F, 806 L, 807 H, 808 N, 810 Q, 812 Y, 813 V, 814 I, 816 D, 817 P, 818 G, 819 I, 821 Y, 822 T, 824 R, 825 G, 826 M, 828 V, 829 F, 831 K and 832 R (here identified by the single-letter code for amino acids) of SEQ ID NO: 2.

The term "part" with regard to the α-glucosidase protein (polypeptide, amino acid sequence) according to the invention encompasses, for the purposes of the present invention, a poly- or oligopeptide composed of at least approximately 10–50, preferably at least 100, more preferably at least 200, especially preferably at least 400 and most preferably approximately 550–675 of the amino acid residues of the α-glucosidase encoded by the nucleic acid molecule according to the invention or its derivatives.

The present invention furthermore relates to a nucleic acid molecule which comprises a nucleic acid molecule of SEQ ID NO: 1 in accordance with the cDNA insert of the plasmid DSM No. 12347 deposited at the DSZM on Jul., 24, 1998, or its derivatives or parts, in particular of the coding region or its derivatives or parts.

The term "derivative" with regard to the nucleic acid molecule (nucleotide sequence or polynucleotide) according to the invention encompasses, for the purposes of this invention, a polynucleotide which comprises at least 478 nucleotides, preferably at least 668, in particular at least 860, and very especially preferably approximately 907–945 nucleotides selected from the group consisting of 4 A, 6A, 12 A, 13 C, 17 G, 25 C, 32 A, 34 C, 38 A, 45 T, 47 A, 49 C, 51 T, 56 G, 62 C, 65 C, 68 T, 73 C, 76 G, 77 G, 78 A, 79 T, 97 G, 100 G, 101 G, 106 A, 108 T, 109 C, 110 A, 111 T, 112G, 113 G, 114 G, 115 G, 116 T, 119 T, 122 T, 125 T, 127 A, 130 A, 131 G, 132 C, 133

A, 134 A, 135 T, 136 G, 137 G, 139 A, 140 T, 141 G, 142 G, 143 A, 144 T, 146 T, 151 T, 152 A, 153 T, 157 G, 158 A, 161 A, 162 T, 164 G, 166 A, 167 T, 169 A, 171 T, 172T, 173 A, 174 C, 175 A, 176 A, 178 G, 179 T, 181 A, 182 T, 183 T, 184 G, 185 G, 187 G, 188 G, 191 T, 193 A, 194 T, 195 T, 196 G, 197 A, 200 T, 202 T, 203 A, 206 T, 208 T, 209 T, 211 G, 212 C, 214 G, 215 G, 216 A, 217 C, 221 C, 223 C, 224 C, 226 G, 232 G, 233 T, 236 T, 237 G, 239 A, 241 C, 242 A, 243 G, 244 T, 247 A, 248 C, 249 T, 254 T, 256 A, 257 T, 259 G, 260 G, 263 G, 265 C, 266 C, 268 G, 269 C, 272 C, 274 A, 275 T, 276 G, 277 C, 278 C, 280 T, 281 A, 283 T, 284 G, 285 G, 289 T, 290 T, 292 G, 293 G, 297 T, 298 C, 299 A, 301 C, 302 A, 304 T, 305 G, 308 G, 310 T, 313 G, 314 G, 316 T, 317 A, 323 A, 324 T, 326 T, 331 G, 332 A, 335 T, 338 A, 343 G, 344 T, 346 G, 347 T, 349 G, 355 T, 356 A, 357 T, 358 G, 359 C, 360 A, 362 A, 365 C, 366 T, 370 A, 371 T, 373 C, 374 C, 377 T, 379 G, 380 A, 382 G, 383 T, 385 A, 386 T, 387 G, 388 T, 389 G, 390 G, 391 A, 392 C, 394 G, 395 A, 397 A, 398 T, 399 T, 400 G, 401 A, 402 T, 403 T, 404 A, 406 A, 407 T, 408 G, 409 G, 410 A, 411 T, 412 G, 415 T, 418 A, 419 A, 421 G, 422 A, 424 T, 425 T, 426 C, 427 A, 428 C, 431 T, 433 G, 434 A, 436 C, 437 C, 439 G, 440 T, 443 A, 445 T, 446 T, 448 C, 449 C, 454 C, 455 A, 459 G, 461 T, 469 T, 470 T, 471 T, 473 T, 478 A, 481 C, 482 T, 484 C, 485 A, 489 G, 490 A, 491 A, 492 T, 493 G, 496 C, 497 A, 499 A, 501 A, 502 T, 503 A, 505 G, 506 T, 511 A, 512 T, 515 T, 517 G, 518 A, 519 T, 520 C, 521 C, 523 G, 524 G, 526 A, 527 T, 536 A, 538 A, 542 C, 544 T, 545 A, 546 T, 547 G, 550 A, 551 C, 553 T, 556 A, 559 A, 560 G, 562 G, 563 G, 565 A, 566 T, 567 G, 569 A, 570 A, 575 A, 576 T, 577 G, 578 T, 580 T, 581 T, 584 T, 586 A, 587 A, 590 G, 593 A, 594 T, 597 T, 601 C, 602 C, 604 T, 605 A, 607 C, 610 G, 611 G, 616 G, 617 T, 619 T, 620 G, 621 G, 622 C, 623 C, 625 G, 626 G, 631 G, 632 T, 634 T, 635 A, 637 T, 640 C, 641 C, 643 G, 644 A, 646 T, 647 T, 650 T, 653 A, 655 C, 656 C, 659 C, 660 T, 662 C, 663 T, 670 T, 671 T, 673 T, 674 G, 675 G, 680 A, 682 G, 683 A, 685 A, 686 T, 689 A, 690 G, 694 T, 695 T, 697 C, 701 A, 704 T, 707 T, 709 C, 710 C, 713 T, 715 G, 716 A, 717 T, 718 G, 719 G, 722 T, 724 T, 725 G, 726 G, 728 T, 730 G, 731 A, 733 A, 734 T, 735 G, 736 A, 737 G, 739 G, 740 A, 745 T, 746 C, 748 A, 749 A, 751 T, 752 T, 754 A, 755 T, 758 C, 759 T, 760 T, 761 C, 764 C, 766 T, 773 C, 778 T, 779 C, 780 T, 782 C, 785 T, 787 G, 788 A, 791 A, 792 T, 793 C, 794 C, 796 C, 797 C, 799 T, 800 A, 802 A, 803 A, 805 A, 806 T, 808 A, 809 A, 811 A, 812 A, 814 T, 815 C, 817 G, 818 A, 820 G, 829 C, 830 C, 832 A, 833 T, 835 A, 841 A, 844 A, 845 C, 848 I, 850 C, 851 C, 854 C, 856 A, 857 C, 860 C, 862 A, 865 A, 866 A, 868 T, 870 T, 871 G, 872 G, 875 A, 883 G, 884 A, 886 T, 887 A, 890 A, 891 T, 892 G, 895 C, 896 A, 897 T, 898 A, 899 A, 902 T, 904 T, 906 T, 907 G, 908 G, 914 T, 916 G, 917 A, 918 A, 920 C, 921 T, 924 A, 925 G, 927 C, 928 A, 929 C, 937 G, 938 C, 941 T, 944 T, 953 C, 958 A, 962 G, 964 C, 965 C, 967 T, 968 T, 971 T, 974 T, 979 A, 980 G, 982 T, 983 C, 985 A, 986 C, 988 T, 989 T, 990 T, 995 G, 997 T, 998 C, 1000 G, 1001 G, 1003 A, 1006 T, 1007 A, 1008 C, 1009 A, 1010 C, 1013 C, 1015 C, 1016 A, 1018 T, 1019 G, 1020 G, 1021 A, 1022 C, 1024 G, 1025 G, 1027 G, 1028 A, 1029 T, 1030 A, 1031 A, 1032 T, 1033 G, 1034 C, 1035 T, 1036 G, 1037 C, 1039 A, 1042 T, 1043 G, 1044 G, 1046 A, 1048 G, 1049 A, 1052 T, 1057 T, 1058 A, 1059 C, 1060 T, 1061 C, 1063 A, 1064 T, 1066 C, 1067 C, 1072 A, 1073 T, 1076 T, 1080 C, 1081 T, 1082 T, 1083 T, 1084 G, 1085 G, 1088 T, 1090 T, 1091 T, 1092 T, 1093 G, 1094 G, 1096 A, 1097 T, 1099 C, 1100 C, 1102 A, 1103 T, 1104 G, 1106 T, 1108 G, 1109 G, 1111 G, 1112 C, 1114 G, 1115 A, 1116 T, 1117 A, 1118 T, 1120 T, 1121 G, 1123 G, 1124 G, 1125 T, 1126 T, 1127 T, 1138 A, 1139 C, 1141 A, 1142 C, 1144 G, 1145 A, 1147 G, 1148 A, 1151 T, 1153 T, 1154 G, 1157 G, 1159 C, 1160 G, 1162 T, 1163 G, 1164 G, 1165 A, 1166 T, 1168 C, 1169 A, 1170 G, 1171 C, 1172 T, 1174 G, 1175 T, 1177 G, 1178 C, 1180 T, 1181 T, 1183 T, 1184 A, 1186 C, 1187 C, 1189 T, 1190 T, 1193 C, 1195 A, 1196 G, 1198 G, 1199 A, 1201 C, 1202 A, 1204 T, 1205 C, 1208 C, 1213 G, 1216 A, 1217 C, 1220 C, 1225 C, 1226 A, 1228 G, 1229 A, 1231 C, 1232 T, 1234 T, 1235 A, 1240 T, 1241 G, 1242 G, 1243 G, 1244 A, 1246 T, 1247 C, 1249 G, 1250 T, 1252 G, 1253 C, 1254 T, 1256 C, 1259 C, 1261 G, 1262 C, 1264 A, 1267 A, 1270 G, 1271 T, 1274 T, 1276 G, 1277 G, 1279 C, 1280 T, 1281 C, 1283 G, 1292 T, 1294 C, 1295 T, 1297 C, 1298 T, 1301 A, 1306 T, 1307 A, 1309 A, 1313 T, 1315 A, 1316 T, 1317 G, 1318 T, 1319 A, 1321 G, 1322 A, 1324 G, 1325 C, 1328 A, 1331 T, 1333 A, 1336 G, 1337 G, 1339 A, 1342 C, 1343 C, 1345 A, 1346 T, 1348 G, 1349 C, 1351 C, 1352 G, 1354 C, 1355 C, 1357 C, 1358 T, 1360 T, 1362 C, 1363 T, 1364 T, 1367 C, 1369 T, 1370 T, 1372 C, 1373 C, 1376 A, 1378 G, 1379 A, 1387 A, 1388 C, 1390 T, 1393 G, 1396 A, 1397 T, 1403 C, 1405 C, 1406 A, 1407 G, 1408 T, 1409 T, 1412 T, 1415 T, 1417 G, 1418 G, 1420 A, 1422 A, 1424 G, 1427 C, 1429 A, 1430 T, 1431 G, 1433 T, 1435 T, 1436 C, 1438 C, 1439 C, 1444 C, 1445 T, 1448 A, 1450 C, 1453 G, 1454 G, 1456 G, 1463 C, 1465 G, 1466 T, 1470 T, 1471 G, 1472 C, 1474 T, 1475 A, 1477 T, 1480 C, 1481 C, 1486 G, 1487 G, 1488 A, 1489 A, 1490 A, 1492 T, 1493 G, 1494 G, 1496 T, 1501 C, 1502 T, 1504 T, 1508 A, 1510 T, 1511 A, 1514 C, 1520 C, 1522 G, 1523 T, 1527 T, 1533 T, 1537 G, 1538 G, 1540 A, 1544 A, 1547 T, 1549 A, 1552 C, 1559 C, 1561 C, 1562 C, 1565 C, 1567 G, 1568 A, 1569 T, 1570 C, 1571 A, 1575 T, 1577 A, 1578 A, 1579 G, 1580 T, 1582 C, 1583 A, 1586 T, 1588 C, 1591 G, 1592 A, 1593 A, 1594 G, 1595 G, 1597 A, 1600 A, 1601 T, 1604 T, 1605 G, 1606 G, 1609 A, 1610 T, 1611 G, 1612 C, 1613 A, 1614 A, 1615 G, 1616 G, 1619 A, 1621 G, 1622 C, 1625 T, 1626 G, 1627 A, 1628 C, 1630 A, 1631 C, 1636 G, 1639 G, 1640 C, 1645 A, 1648 A, 1649 C, 1652 C, 1654 T, 1658 A, 1660 C, 1661 T, 1664 T, 1665 G, 1667 T, 1669 G, 1670 T, 1675 A, 1676 G, 1689 C, 1690 A, 1692 C, 1696 G, 1697 G, 1699 G, 1700 A, 1703 C, 1705 T, 1706 T, 1709 T, 1711 G, 1712 A, 1715 A, 1717 G, 1724 A, 1727 T, 1732 A, 1733 T, 1735 G, 1736 G, 1745 G, 1746 A, 1747 G, 1748 G, 1750 A, 1753 T, 1754 G, 1755 G, 1756 A, 1757 C, 1760 T, 1762 G, 1763 T, 1765 A, 1768 T, 1769 T, 1775 G, 1776 C, 1781 T, 1783 A, 1789 A, 1796 T, 1802 T, 1807 T, 1808 C, 1809 A, 1810 G, 1811 A, 1813 G, 1814 T, 1816 G, 1817 T, 1828 T, 1830 T, 1831 G, 1832 C, 1836 G, 1845 A, 1846 T, 1848 G, 1851 C, 1853 T, 1855 G, 1858 A, 1859 A, 1862 T, 1864 A, 1865 C, 1868 T, 1871 T, 1873 G, 1874 G, 1876 T, 1877 T, 1881 A, 1890 A, 1894 T, 1897 A, 1901 G, 1908 G, 1925 A, 1929 A, 1945 A, 1953 T, 1958 A, 1966 G, 1972 T, 1973 T, 1976 T, 1984 G, 1988 T, 1990 T, 1991 C, 1997 C, 2006 T, 2009 T, 2011 G, 2012 G, 2020 T, 2021 T, 2024 A, 2027 T and 2033 T of SEQ ID NO: 1 and which furthermore comprises at least approximately 1–93 nucleotides, preferably at least 187, in particular 261, more preferably at least 336 and very especially preferably approximately 354–369 nucleotides selected from the group consisting of 1 C, 10 A, 16 A, 19 G, 21 T, 23 A, 24 C, 26 C, 30 A, 33 A, 36 C, 39 T, 43 A, 48 G, 52 C, 53 A, 54 C, 57 T, 58 C, 59 C, 60 G, 63 G, 64 G, 66 G, 67 C, 69 C, 70 C, 71 A, 72 C, 74 G, 75 G, 80 A, 81 C, 86 T, 88 C, 89 G, 91 T, 93 C, 94 T, 96 C, 99 C, 102 A, 103 G, 104 T, 105 T, 107 G, 123 T, 128 G, 138 C, 145 A, 149 T, 156 G, 170 G, 189 G, 190 T, 192 A, 199 T, 201 G, 264 T, 271 G, 279 A, 291 C, 294 A, 309 G, 325 A, 327 T, 328 G, 333 T, 334 G, 340 C, 341 T, 342 G, 348 G, 354 T, 363 G, 364 T, 375 G, 384 T, 420 G, 429 A, 432 C, 438 A, 444 C, 456 G, 457 C, 458 G, 460 G, 462 A, 464 T, 465 T, 467 T, 468 T, 472 C, 476 G, 477 G, 480 G, 486 T, 487 C, 494 A, 507 A, 513 A, 514 G, 516 A, 522 A, 525 A, 534 C, 537 C, 540 T, 543 A, 549 C, 552 C, 557 G, 558 G, 564 C, 573 A, 592 G, 595 A, 596 A, 599 T, 603 C, 608 A, 609 A, 612 G, 614 T, 627 G, 636 T, 639 T, 651 A, 661 A, 665 A, 667 G, 668 T, 669 A, 678 A, 687 T, 688 G, 692 A, 706 G, 708 A, 727 C, 744 G, 771 A, 774 A, 775 T, 776 C, 783 C, 784 T, 798 C, 807 A, 813 C, 819 C, 825 C, 834 C, 838 T, 842 G, 843 A, 855 C, 858 T, 863 C, 864 A, 878 C, 879 A, 881 T, 882 G, 885 G, 888 T, 903 T, 912 A, 931 T, 934 A, 935 G, 940 T, 949 G, 954 T, 957 T, 976 G, 971 T, 987 T, 991 C, 1002 C, 1004 G, 1012 T, 1038 T, 1041 C, 1062 C, 1068 T, 1079 G, 1087 T, 1095 A, 1132 A, 1140 T, 1161 C, 1167 T, 1179 A, 1188 A, 1203 C, 1206 T, 1210 A, 1211 A, 1212 G, 1215 C, 1223 C, 1224 C, 1239 T, 1258 G, 1263 C, 1265 A, 1275 T, 1278 G, 1287 T, 1288 C, 1291 T, 1293 A, 1296 T, 1305 T, 1310 T, 1311 G, 1312 C, 1314 T, 1330 A, 1338 G, 1340 C, 1341 T, 1344 C, 1347 T, 1353 A, 1356 C, 1386 G, 1389 A, 1391 T, 1402 A, 1416 C, 1432 A, 1441 A, 1443 A, 1446 T, 1455 A, 1459 A, 1460 C, 1461 C, 1467 T, 1497 T, 1500 C, 1503 C, 1518 C, 1521 T, 1528 T, 1530 G, 1531 A, 1534 C, 1535 A, 1546 A, 1557 C, 1563 A, 1566 A, 1575 A, 1581 A, 1590 T, 1596 G, 1602 A, 1603 T, 1607 T, 1608 C, 1632 A, 1641 T, 1643 A, 1644 G, 1650 T, 1651 G, 1653 A, 1657 A, 1659 A, 1665 T, 1668 C, 1672 C, 1678 A, 1680 C, 1681 A, 1683 C, 1684 A, 1695 A, 1698 A, 1704 A, 1708 G, 1718 A, 1719 C, 1738 A, 1743 G, 1749 G, 1751 G, 1752 G, 1758 G, 1761 A, 1772 A, 1773 C, 1774 A, 1784 T, 1786 T, 1788 C, 1791 T, 1792 A, 1795 A, 1800 G, 1801 G, 1803 T, 1805 A, 1812 G, 1815 T, 1825 C, 1834 C, 1837 G, 1842 A, 1843 G, 1847 T, 1852 C, 1857 A, 1869 A, 1875 A, 1878 T, 1884 T, 1886 T, 1891 G, 1895 T, 1896 G, 1902 C, 1903 T, 1904 A, 1905 T, 1906 G, 1909 C, 1911 T, 1913 T, 1914 T, 1915 G, 1918 T, 1919 C, 1920 A, 1922 A, 1923 C, 1924 C, 1932 G, 1936 A, 1940 C, 1948 G, 1949 A, 1955 T, 1957 A, 1959 G, 1960 C, 1962 G, 1964 G, 1969 C, 1975 G, 1979 C, 1981 A, 1986 A, 1989 C, 1995 G, 1996 A, 2001 A, 2002 A, 2005 T, 2007 G, 2008 A, 2035 T, 2038 A, 2040 C, 2042 T, 2044 A, 2045 C, 2046 T, 2047 T and 2048 A of SEQ ID NO: 1.

In the numbering of the positions of the individual elements of the nucleotide or amino acid sequences according to the invention of SEQ ID NO: 1 or SEQ ID NO: 2, which has been stated above explicitly, derivatives of said sequences according to the invention are also to be understood as meaning those sequences in which the numbering of the individual sequence elements may deviate from those of the SEQ ID NOS: 1 or 2 according to the invention. What is decisive here is significant agreement of at least one sequence section ("part") with the sequence according to the invention. Such agreements can be determined in a simple manner using general expert knowledge, for example by making use of suitable computer programs, for example by carrying out a sequence comparison of the sequence according to the invention with a sequence in question to be compared (so-called sequence alignment). Such computer programs, which, for example, are commercially available (for example Omiga®, Version 1.1.3. by Oxford Molecular Ltd., Oxford, UK) and which in some cases are also an integral component of sequence databases (for example EMBL, GenBank), identify, for example, the best-possible agreement of identical, or, if appropriate, chemical equivalent, sequence elements and take into consideration in particular the existence of insertions and/or deletions which may lead to a shift of individual sequence elements or of sequence sections and which can thus affect numbering of the sequence elements or sequence sections.

With regard to the nucleic acid molecule according to the invention which encodes an α-glucosidase, the term "derivative" furthermore encompasses a nucleic molecule which deviates from SEQ ID NO: 1 by addition, deletion, insertion or recombination of one or more nucleotides and which meets the conditions as defined above.

With regard to the nucleic acid molecule according to the invention which encodes an α-glucosidase, the term "derivative" furthermore comprises a complementary or inverted-complementary sequence (polynucleotide) of the nucleic acid molecule according to the invention or of derivatives or parts thereof.

The term "part", which refers to the nucleic acid molecule according to the present invention which encodes an α-glucosidase, encompasses a poly- or oligonucleotide composed of at least approximately 15–35, preferably at least approximately 36–100, in particular at least 200, more preferably at last 400, especially preferably at least 800 and most preferably approximately 1400–1700 of the nucleotides of a nucleic acid molecule according to the invention which encodes an α-glucosidase, or their derivatives.

In a preferred embodiment of the present invention, the terms "derivative" and/or "part" according to the present invention encompass a polynucleotide, or a poly- or oligopeptide as defined above, which shows functional and/or structural equivalence of the α-glucosidase gene obtained from potato (i.e. of the nucleic acid molecule which encodes the α-glucosidase) or α-glucosidase polypeptide. The term "functional and/or structural equivalence" generally means the same, an equivalent or similar function of the inventive molecule in question, if appropriate especially biological function.

The invention furthermore relates to a recombinant nucleic acid molecule comprising a) a nucleotide sequence encoding a protein with the function of an α-glucosidase, preferably from potato, or parts of said nucleotide sequence, and b) one or more nucleotide sequences which encode a protein selected from amongst group A, composed of proteins with the function of branching enzymes, ADP glucose pyrophosphorylases, granule-bound starch synthases, soluble starch synthases, debranching enzymes, disproportioning enzymes, plastid starch phosphorylases, R1 enzymes, amylases, glucosidases, parts of nucleotide sequences encoding proteins selected from amongst group A and nucleic acid molecules which hybridize with one of said nucleotide sequences or parts thereof, preferably a deoxyribonucleic acid or ribonucleic acid molecule, especially preferably a cDNA molecule. Especially preferred is a nucleic acid molecule which specifically hybridizes with one of said nucleotide sequences or parts thereof.

The nucleotide sequence according to the invention encoding a protein with the function of a potato α-glucosidase is depicted by SEQ ID NO: 1, the protein encoded by the nucleotide sequence by SEQ ID NO:2.

SEQ ID NO: 1
cgaatacgaataaccgacgctaaccatcaacgatgggaagtgccggaagaaattctccac
cgtccaccaccgccgtcgccgccgtcaacctccaactcctcatcagaaaaccactcccca
attaccctctctaacccaaactcagacctagagttcaccttcacaacaccatcccattc
agcttcaccgtccgccggcgctccaccggggatactcttttcgatacttcgccggagtta
gtcatgggttttgcttctgagtagcaatggcatggatattgtgtatacgggtgatagga
ttagttacaaggtgattggagggttaattgatttgtatttctttgccggaccttcgccgg
aaatggtggtggatcagtatactcagcttattggtcgtcctgctgctatgccatattggt
ctttcggatttcaccaatgccggtggggttacaagaatattgatgatgttgaactggtag
tggatagttatgcaaagtctagaataccgctggaggttatgtggactgatattgattaca
tggatggttttaaggacttcacactcgatccagttaacttcccactggagcgggtaattt
ttttctcaggaagcttcatcagaatgatcagaaatatgtactaatagtagatccaggaa
ttagcatcaacaatacatatgacacctataggagaggcatggaagcagatgtcttcataa
aacgcgataatatgccctaccaaggggttgtttggccagggaatgtttattatcctgatt
ttctaaatccagctactgaagtattttggagaaatgaaattgagaagttccaggatctcg
taccttttgatggcctgtggcttgacatgaatgaattgtcaaacttcataacttcccctc
ctacaccatcatctacctttgatgatcctccctacaagataaacaactctggcgatcact
tgcccatcaattatagaacagttccagccacttctacacattttggtgatacaatggagt
ataatgtccataaccttatggattacttgaatctagagccacttatagtgcattggtta
atgtcactggtaaaaggccattcattcttgtaagatcaacttttcttggctctggcagat
acacgtcacattggactggagataatgctgctacctggaacgatttggcatactccattc
ctactatcttgagctttggattgtttggaattccaatggttggagctgatatatgtggtt
tttcaagtaacactactgaagagctttgccgccgctggattcagcttggagcattctatc
catttgcaagagaccactctgctaaggacacaaccccccaagagctctatagttgggatt
cagttgctgcagcagccaagaaagtccttgggctccgatatcagttacttccatactttt
atatgcttatgtacgaggcacatataaaagggactcccattgcacgacccctcttcttct
ctttccctcaagatgccaagacatttgatatcagcacacagttccttctcggtaaaggtg
tcatgatctcacctatacttaagcaaggagcaacctctgttgatgcatatttccctgctg
gaaactggtttgacctcttcaattactctcgctctgtgagtttgaatcaaggaacatata
tgacacttgacgcaccaccagatcatataaatgtacatgttcgtgaagggaacatattgg
tcatgcaaggggaagcaatgacaacacaagctgctcagaggactgcattcaaactccttg
tcgtgctgagcagcagcaaaaacagcacaggagaactatttgtggacgatgacgatgagg
tgcagatgggaagagagggagggaggtggacgctagttaagtttaacagcaatatcattg
gcaataaaattgtggttaaatcagaggttgtgaatggacgatatgcgctggatcaaggat
tggtccttgaaaaggtgacattattgggatttgaaaatgtgagaggattgaagagctatg
agcttgttggatcacaccagcaagggaacacaacaatgaaggaaagtcttaagcagagtg
gacagtttgttactatggaaatctcagggatgtcaatattgatagggaaagagttcaaat
tggagctatacatcattactaacaaatgaattaagttatatacgcttgttgtatgaaat
tttctttcatttatcaatgcagtttaatttatgataaaaaaaaaaaaaaaaa

SEQ ID NO: 2
PKLRPRVHPSQHHPIQLHRPPALHRGYSFRYFAGVSHGVLLLSSNGMDIVYTGDRISYKV

```
-continued
IGGLIDLYFFAGPSPEMVVDQYTQLIGRPAAMPYWSFGFHQCRWGYKNIDDVELVVDSYA

KSRIPLEVMWTDIDYMDGFKDFTLDPVNFPLERVIFFLRKLHQNDQKYVLIVDPGISINN

TYDTYRRGMEADVFIKRDNMPVQGVVWPGNVYYPDFLNPATEVFWRNEIEKFQDLVPFDG

LWLDMNELSNFITSPPTPSSTFDDPPYKINNSGDHLPINYRTVPATSTHFGDTMEYNVHN

LYGLLESRATYSALVNVTGKRPFILVRSTFLGSGRYTSHWTGDNAATWNDLAYSIPTILS

FGLFGIPMVGADICGFSSNTTEELCRRWIQLGAFYPFARDHSAKDTTPQELYSWDSVAAA

AKKVLGLRYQLLPYFYMLMYEAHIKGTPIARPLFFSFPQDAKTFDISTQFLLGKGVMISP

ILKQGATSVDAYFPAGNWFDLFNYSRSVSLNQGTYMTLDAPPDHINVHVREGNILVMQGE

AMTTQAAQRTAFKLLVVLSSSKNSTGELFVDDDDEVQMGREGGRWTLVKFNSNIIGNKIV

VKSEVVNGRYALDQGLVLEKVTLLGFENVRGLKSYELVGSHQQGNTTMKESLKQSGQFVT

MEISGMSILIGKEFKLELYIIT
```

The α-glucosidase nucleotide sequence according to the invention shows relatively little sequence homology with known α-glucosidase-encoding molecules (Taylor et al., 1998, Plant J. 13: 419–424, Sugimoto et al., 1997, Plant Mol. Biol. 33, 765–768; EMBL Datenbank-Einträge: U22450, P10253, D86624). The amino acid sequence differs markedly from the α-glucosidases described in the prior art, in particular in the 5' region, as can be seen from a sequence alignment with SEQ ID NO: 2.

Nucleotide sequences which encode a protein of group A and which are suitable according to the invention have been described, for example, for soluble (types I, II, III or IV) or granule-bound starch synthase isoforms in Hergersberg, 1988, Ph.D. thesis, University of Cologne; Abel, 1995, Ph.D. thesis, FU Berlin; Abel et al., 1996, Plant Journal 10(6):981–991; Visser et al., 1989, Plant Sci. 64:185–192; van der Leij et al., 1991, Mol. Gen. Genet. 228:240–248; EP-A-0779363; WO 92/11376; WO 96/15248; WO 97/26362; WO 97/44472; WO 97/45545; Delrue et al., 1992, J. Bacteriol. 174: 3612–3620; Baba et al., 1993, Plant Physiol. 103:565–573; Dry et al., 1992, The Plant Journal 2,2: 193–202 or else in the EMBL database entries X74160; X58453; X88789; X 94400; for branching enzyme isoforms (branching enzymes I, IIa or IIb), debranching enzyme isoforms (debranching enzyme, isoamylases, pullulanases, R1 enzymes) or disproportioning enzyme isoforms, for example, described in WO 92114827; WO 95107335; WO 95/09922; WO 96/19581; WO 97/22703; WO 97/32985; WO 97/42328; Takaha et al., 1993, J. Biol. Chem. 268: 1391–1396 or else in the EMBL database entry X83969, and those for ADP glucose pyrophosphorylases and plastid starch phosphorylase isoforms, for example, described in EP-A-0368506; EP-A-0455316; WO 94/28146; DE 19653176.4; WO 97/11188; Brisson et al., 1989, The Plant Cell 1:559–566; Buchner et al., 1996, Planta 199:64–73; Camirand et al., 1989, Plant Physiol. 89(4 Suppl.) 61; Bhatt & Knowler, J. Exp. Botany 41 (Suppl.) 5–7; Lin et al., 1991, Plant Physiol. 95: 1250–1253; Sonnewald et al., 1995, Plant Mol. Biol. 27:567–576; DDBJ No. D23280; Lorberth et al., 1998, Nature Biotechnology 16:473–477.

The nucleotide sequences to be employed suitably in accordance with the invention are of pro- or eukaryotic origin, preferably of bacterial, fungal or plant origin.

The term "parts of nucleotide sequences" denotes, for the purposes of the present invention, parts of the nucleotide sequences to be used in accordance with the invention which are at least 15 bp, preferably at least 150 bp, especially preferably at least 500 bp in length, but which do not exceed a length of 5000 bp, preferably 2500 bp.

The term "hybridization" means, for the purposes of the present invention, hybridization under conventional hybridization conditions, preferably under stringent conditions, as are described, for example, in Sambrook et al., Molecular Cloning, A Laboratory Manual, 2nd Ed. (1989) Cold Spring Harbor Laboratory Press, Cold Spring Harbor, N.Y.).

A "specific hybridization" especially preferably takes place under the following highly stringent conditions: Hybridization buffer: 2×SSC; 10×Denhardt solution (Fikoll 400+PEG+BSA; ratio 1:1:1); 0.1% SDS; 5 mM EDTA; 50 mM $Na_2HPO_4$; 250 µg/ml herring sperm DNA; 50 µg/ml tRNA; or 0.25 M sodium phosphate buffer pH 7.2; 1 mM EDTA; 7% SDS at a

| | |
|---|---|
| Hybridization temperature: | T = 55 to 68° C., |
| Wash buffer: | 0.2 × SSC; 0.1% SDS and |
| Wash temperature: | T = 40 to 68° C.. |

The molecules which hybridize with the nucleic acid molecules according to the invention also encompass fragments, derivatives and allelic variants of the nucleic acid molecules according to the invention. Fragments are to be understood as meaning parts of the nucleic acid molecules which are long enough to encode a functionally active part of the proteins described. The term derivative means in this context that the sequences of these molecules differ from the sequences of the nucleic acid molecules according to the invention in one or more positions and exhibit a high degree of homology to these sequences. Homology means a sequence identity of at least 60%, preferably over 70% and especially preferably over 85%. The deviations relative to the nucleic acid molecules according to the invention may have originated by means of deletions, substitutions, insertions or recombinations.

Homology furthermore means that functional and/or structural equivalence exists between the nucleic acid molecules in question or the proteins encoded by them. The nucleic acid molecules which are homologous to the molecules according to the invention and which constitute derivatives of these molecules are, as a rule, variations of these molecules which constitute modifications which exert the same biological function. They may be naturally occurring variations, for example sequences from other plant species, or mutations, it being possible for these mutations to have occurred naturally or to have been introduced by directed mutagenesis. The variations may further be synthetic sequences. The allelic variants may be naturally occurring variants or else synthetic variants or variants generated by recombinant DNA technology.

The nucleic acid molecules according to the invention may be DNA molecules, in particular cDNA or genomic molecules. The nucleic acid molecules according to the invention may furthermore be RNA molecules. The nucleic acid molecules according to the invention or parts thereof can have been obtained, for example, from natural sources or generated by means of recombinant technology or by synthesis.

To express the nucleic acid molecules according to the invention in sense or antisense orientation in plant cells, they are linked to regulatory DNA elements which ensure transcription in plant cells. These include, in particular, promoters. In general, any promoter which is active in plant cells is suitable for expression. The promoter may have been chosen in such a way that expression is constitutive or only in a particular tissue, at a particular point in time of plant development or at a point in time determined by external factors which can be, for example, chemically or biologically inducible. Relative to the transformed plant, the promoter—and also the nucleotide sequence—can be homologous or heterologous. Examples of suitable promoters are the cauliflower mosaic virus 35S RNA promoter for constitutive expression, the patatin gene promoter B33 (Rocha-Sosa et al., 1989, EMBO J. 8:23–29) for tuber-specific expression in potatoes or a promoter which ensures expression only in photosynthetically active tissues, for example the ST-LS1 promoter (Stockhaus et al., 1987, Proc. Natl. Acad. Sci. USA 84: 7943–7947; Stockhaus et al., 1989, EMBO J. 8: 2445–2451) or, for endosperm-specific expression, the wheat HMG promoter or promoters from maize zein genes.

A termination sequence which terminates the nucleic acid molecule according to the invention may serve to correctly end transcription and to add to the transcript a poly-A tail, which is considered to have a function in stabilizing the transcripts. Such elements have been described in the literature (cf. Gielen et al., 1989, EMBO J. 8:23–29) and are exchangeable as desired.

The nucleic acid molecules according to the invention can be used for generating transgenic plant cells and plants which show an increase or reduction in the activity of α-glucosidase or in the activity of α-glucosidase and at least one further enzyme of starch metabolism. To this end, the nucleic acid molecules according to the invention are introduced into suitable vectors, provided with the regulatory nucleic acid sequences which are necessary for efficient transcription in plant cells, and introduced into plant cells. On the one hand, there is the possibility of using the nucleic acid molecules according to the invention for inhibiting the synthesis of the endogenous α-glucosidase or the endogenous α-glucosidase and at least one further protein of group A in the cells. This can be achieved with the aid of antisense constructs, in-vivo mutagenesis, a cosuppression effect which occurs, or with the aid of suitably constructed ribozymes. On the other hand, the nucleic acid molecules according to the invention can be used for expressing α-glucosidase or α-glucosidase and at least one further protein of group A in the cells of transgenic plants and thus lead to an increased activity in the cells of the enzymes which have been expressed in each case.

In addition, there exists the possibility of using the nucleic acid molecules according to the invention for inhibiting the synthesis of the endogenous α-glucosidase and the overexpression of at least one further protein of group A in the cells.

Finally, the nucleic acid molecules according to the invention can also be used for expressing α-glucosidase and inhibiting at least one further protein of group A in the cells of transgenic plants. The two last-mentioned embodiments of the invention thus lead, in the cells, to a simultaneous inhibition and increase in the activities of the enzymes which are inhibited or expressed, respectively.

The invention furthermore relates to a vector comprising a nucleic acid molecule according to the invention.

The term "vector" encompasses plasmids, cosmids, viruses, bacteriophages and other vectors conventionally used in genetic engineering which contain the nucleic acid molecules according to the invention and which are suitable for transforming cells. Such vectors are preferably suitable for transforming plant cells. Especially preferably, they permit integration of the nucleic acid molecules according to the invention, if appropriate together with flanking regulatory regions, into the genome of the plant cell. Examples are binary vectors, such as pBinAR or pBinB33, which can be employed in agrobacteria-mediated gene transfer.

In a preferred embodiment, the vector according to the invention is distinguished by the fact that the nucleotide sequence encoding a protein with the function of an α-glucosidase or parts thereof is present in sense or antisense orientation.

In a further preferred embodiment, the vector according to the invention is distinguished by the fact that the nucleotide sequence which encodes one or more proteins selected from amongst group A or parts thereof is present in sense or antisense orientation.

In yet a further preferred embodiment, the vector according to the invention is distinguished by the fact that the nucleotide sequence which encodes a plurality of proteins selected from group A or parts thereof is present partly in sense and partly in antisense orientation.

Very especially preferably, the vector according to the invention is linked to regulatory elements which ensure expression in a prokaryotic or eukaryotic cell, i.e., for example, transcription and synthesis of an RNA which, if the nucleotide sequence is present in sense orientation, is translatable.

In addition, it is possible to introduce, by means of customary techniques of molecular biology (see, for example, Sambrook et al., 1989, Molecular Cloning, A Laboratory Manual, 2nd Ed. Cold Spring Harbor Laboratory Press, Cold Spring Harbour, N.Y.), various mutations into the DNA sequences according to the invention, which leads to the synthesis of proteins with biological properties which may have been modified. On the one hand, it is possible to generate deletion mutants in which sequences are generated, by progressive deletions from the 5' or the 3' end of the coding DNA sequences which lead to the synthesis of analogously truncated proteins. For example, such deletions at the 5' end of the DNA sequence allow the targeted production of enzymes which, due to the removal of the relevant transit or signal sequences, are no longer localized in their original (homologous) compartment, but in the cytosol, or which, due to the addition of other signal sequences, are localized in one or more other (heterologous) compartments.

On the other hand, it is also feasible to introduce point mutations in positions where an altered amino acid sequence affects, for example, the enzyme activity or the regulation of the enzyme. Thus, it is possible, for example, to generate mutants which have an altered $K_M$ or $k_{cat}$ value or which are no longer subject to the regulatory mechanisms normally present in the cell via allosteric regulation or covalent modification.

For the purposes of recombination manipulation in prokaryotic cells, the DNA sequences according to the invention or parts of these sequences can be introduced into plasmids which permit mutagenesis or an altered sequence by the recombination of DNA sequences. Base exchanges may be performed or natural or synthetic sequences may be added, with the aid of standard methods in molecular biology (cf. Sambrook et al., 1989, loc. cit.). To link the DNA fragments to each other, adapters or linkers may be attached to the fragments. Furthermore, manipulations which provide suitable restriction cleavage sites or which remove excessive DNA or restriction cleavage sites which are no longer needed may be employed. Where insertions, deletions or substitutions are suitable, in-vitro mutagenesis, primer repair, restriction or ligation may be used. The analytical methods which are generally employed are sequence analysis, restriction analysis and, if appropriate, other methods of biochemistry and molecular biology.

The invention furthermore relates to a host cell, in particular prokaryotic or eukaryotic cells, preferably bacterial or plant cells (for example from E. coli, Agrobacterium, Solananceae, Poideae, rye, barley, oats, maize, wheat, sorghum and millet, sago, rice, peas, marrowfat peas, cassava, potatoes, tomatoes, oilseed rape, soybeans, hemp, flax, sunflowers, cowpeas, mung beans, beans, bananas or arrowroot) which contains a nucleic acid molecule according to the invention or a vector according to the invention or which is derived from a cell which has been transformed with a nucleic acid molecule according to the invention or a vector according to the invention.

The invention furthermore relates to host cells, in particular prokaryotic or eukaryotic cells, preferably bacterial or plant cells (for example of E. coli, Agrobacterium, Solanaceae, Poideae, rye, barley, oats, maize, wheat, sorghum and millet, sago, rice, peas, marrowfat peas, cassava, potatoes, tomatoes, oilseed rape, soybeans, hemp, flax, sunflowers, cowpeas, mung beans, beans, bananas or arrowroot) which contains, in addition to a recombinant nucleic acid molecule encoding a protein with the function of a β-amylase, one or more further recombinant nucleic acid molecules which encode a protein selected from group A or their parts or nucleotide sequences hybridizing with these nucleic acid molecules.

In addition to using the nucleic acid molecules according to the invention, the host cells according to the invention may, if appropriate, also be generated by successive transformation (so-called supertransformation), by employing individual nucleotide sequences or vectors comprising nucleotide sequences which encode a protein with the function of branching enzymes, ADP glucose pyrophosphorylases, granule-bound starch synthases, soluble starch synthases I, II, III or IV, debranching enzymes, disproportioning enzymes, plastid starch phosphorylases, R1 enzymes, amylases, glucosidases, parts thereof, and nucleic acid molecules which hybridizes with one of said nucleotide sequences or their parts, in a plurality of successive cell transformations. A further embodiment of the present invention relates to a method of generating a transgenic plant cell which synthesizes a modified starch, which comprises integrating a nucleic acid molecule according to the invention or a vector according to the invention into the genome of a plant cell.

Providing the nucleic acid molecules according to the invention makes it possible to engage in the start metabolism of plants, with the aid of recombinant methods, and to alter it in such a way that the result is the synthesis of a modified starch which is altered relative to the starch synthesized in the wild-type plant with regard to, for example, structure, water content, protein content, lipid content, fiber content, ash/phosphate content, amylase/amylopectin ratio, molecular mass distribution, degree of branching, granule size, granule shape and crystallization, or else in its physicochemical properties such as the viscoelasticity, the sorptive characteristics, gelatinization temperature, viscosity, thickening capacity, solubility, gel structure, transparency, thermal stability, shear stability, stability to acids, tendency to undergo retrogradation, gelling, freeze-thaw stability, complex formation, iodine binding, film formation, adhesion power, enzyme stability, digestibility or reactivity. There is also the possibility of increasing the yield in suitably genetically modified plants by increasing the activity of proteins which are involved in starch metabolism, for example by overexpressing suitable nucleic acid molecules, or by providing mutants which are no longer subject to the cell's regulatory mechanisms and/or which exhibit different temperature dependencies relating to their activity. A particularly pronounced increase in yield may be the result of increasing the activity of one or more proteins which are involved in the starch metabolism in specific cells of the starch-storing tissue of transformed plants such as, for example, in the tuber in the case of potatoes or in the endosperm of maize or wheat. The economic importance and the advantages of these possibilities of engaging in the starch metabolism are obvious.

When expressing the nucleic acid molecules according to the invention in plants it is possible, in principle, for the protein synthesized to be localized in any desired compartment of the plant cell. To achieve localization in a particular compartment (cytosol, vacuole, apoplast, plastids, mitochondria), the transit or signal sequence which ensures localization must, if necessary, be deleted (removed) and the remaining coding region must, if necessary, be linked to DNA sequences which ensure localization in the compartment in question. Such sequences are known (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The generation of plant cells with a reduced activity of a protein involved in the starch metabolism can be achieved, for example, by expressing a suitable antisense RNA, a sense RNA for achieving a cosuppression effect, in-vivo mutagenesis or by expressing a suitably constructed ribozyme which specifically cleaves transcripts which encode one of the proteins involved in starch metabolism, using a nucleic acid molecule according to the invention, preferably by expressing an antisense transcript.

To this end, it is possible to use, firstly, a DNA molecule which encompasses all of the sequence which encodes a protein involved in starch metabolism including any flanking sequences, as well as DNA molecules which only encompass parts of the coding sequence, these parts having a minimum length of 15 bp, preferably of at least 100–500 bp, and in particular over 500 bp. As a rule, DNA molecules are used which are shorter than 5000 bp, preferably shorter than 2500 bp.

It is also possible to use DNA sequences which exhibit a high degree of homology to the sequences of the DNA molecules according to the invention, but are not fully identical with them. The minimum homology should exceed approx. 65%. The use of sequences with a homology of 75% and in particular 80% is to be preferred.

The expression of ribozymes for reducing the activity of specific proteins in cells is known to the skilled worker and described, for example, in EP-B10 321 201. The expression of ribozymes in plant cells was described, for example, in Feyter et al. (Mol. Gen. Genet. 250 (1996), 329–338).

Furthermore, the reduction of the proteins involved in the starch metabolism in the plant cells according to the invention can also be achieved by so-called "in-vivo mutagenesis", where an RNA-DNA hybrid oligonucleotide ("chimeroplast") is introduced into cells by cell transformation (Kipp P. B. et al., Poster Session at the "5th International Congress of Plant Molecular Biology, 21–27, Sept. 1997, Singapore; R. A. Dixon and C. J. Amtzen, Meeting report on "Metabolic Engineering in Transgenic Plants", Keystone Symposia, Copper Mountain, Colo., USA, TIBTECH 15 (1997), 441–447; international patent application WO 95/15972; Kren et al., Hepatology 25 (1997), 1462–1468; Cole-Strauss et al., Science 273 (1996), 1386–1389).

Part of the DNA component of the RNA-DNA oligonucleotide used for this purpose is homologous to a nucleic acid sequence of an endogenous protein, but exhibits a mutation in comparison with the nucleic acid sequence of the endogenous protein or comprises a heterologous region enclosed by the homologous regions.

Base pairing of the homologous regions of the RNA-DNA oligonucleotide and of the endogenous nucleic acid molecule followed by homologous recombination allows the mutation or heterologous region contained in the DNA component of the RNA-DNA oligonucleotide to be transferred into the genome of a plant cell. This leads to a reduced activity of the protein involved in the starch metabolism.

As an alternative, the enzyme activities which are involved in the starch metabolism can be reduced in the plant cells by a cosuppression effect. This method is known to the skilled worker and is described, for example, by Jorgensen (Trends Biotechnol. 8 (1990), 340–344), Niebel et al., (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al., (Mol. Gen. Genet. 248 (1995), 311–317), de Borne et al. (Mol. Gen. Genet. 243 (1994), 613–621) and other sources.

To inhibit the synthesis, in the transformed plants, of a plurality of enzymes involved in starch biosynthesis, it is possible to use DNA molecules for transformation which simultaneously contain, in antisense orientation and under the control of a suitable promoter, a plurality of regions which encode the relevant enzymes. Each sequence may be under the control of its own promoter, or, alternatively, the sequences can be transcribed by a joint promoter as a fusion, so that synthesis of the proteins in question is inhibited to approximately the same or to a different extent. As regards the length of the individual coding regions which are used in such a construct, what has already been said above for the generation of antisense constructs also applies here. In principle, there is no upper limit for the number of antisense fragments transcribed starting from a promoter in such a DNA molecule. However, the resulting transcript should not, as a rule, exceed a length of 25 kb, preferably 15 kb.

The nucleic acid molecules according to the invention make it possible to transform plant cells and simultaneously to inhibit the synthesis of a plurality of enzymes.

Moreover, it is possible to introduce the nucleic acid molecules according to the invention into traditional mutants which are deficient or defective with regard to one or more starch biosynthesis genes (Shannon and Garwood, 1984, in Whistler, BeMiller and Paschall, Starch: Chemistry and Technology, Academic Press, London, 2nd Edition: 25–86). These defects can relate, for example, to the following proteins: granule-bound (GBSS I) and soluble starch synthases (SSS I, I, III and IV), branching enzymes (BE I, IIa and IIb), debranching enzymes (R-enzymes, isoamylases, pullulanases), disproportioning enzymes and plastid starch phosphorylases.

The present invention thus also relates to transgenic plant cells obtainable by a process according to the invention which have been transformed with a nucleic acid molecule or vector according to the invention, and to transgenic plant cells derived from cells transformed in this way. The cells according to the invention contain a nucleic acid molecule according to the invention, this preferably being linked to regulatory DNA elements which ensure transcription in plant cells, in particular to a promoter. The cells according to the invention can be distinguished from naturally occurring plant cells, inter alia, by the fact that they contain a nucleic acid molecule according to the invention which does not occur naturally in these cells, or by the fact that such a molecule exists integrated at a location in the cell's genome where it does not occur otherwise, i.e. in a different genomic environment. Furthermore, the transgenic plant cells according to the invention can be distinguished from naturally occurring plant cells by the fact that they contain at least one copy of a nucleic acid molecule according to the invention stably integrated into their genome, if appropriate in addition to copies of such a molecule which occur naturally in the cells. If the nucleic acid molecule(s) introduced into the cells is (are) additional copies to molecules which already occur naturally in the cells, then the plant cells according to the invention can be distinguished from naturally occurring plant cells in particular by the fact that this (these) additional copy (copies) is (are) localized at sites of the genome at which it (they) do(es) not occur naturally. This can be checked, for example, with the aid of a Southern blot analysis.

Preferred plant cells according to the invention are those in which the enzyme activity of individual enzymes which are involved in starch metabolism is increased or reduced by at least 10%, especially preferably by at least 30%, and very especially preferably by at least 50%.

Moreover, the plant cells according to the invention can be distinguished from naturally occurring plant cells preferably by at least one of the following features: if the nucleic acid molecule according to the invention which has been introduced is heterologous relative to the plant cell, the transgenic plant cells exhibit transcripts of the nucleic acid molecules according to the invention which have been introduced. This can be detected by, for example, northern blot analysis. For example, the plant cells according to the invention contain one or more proteins encoded by a nucleic acid molecule according to the invention which has been introduced. This can be detected by, for example, immunological methods, in particular by western blot analysis.

If the nucleic acid molecule according to the invention which has been introduced is homologous relative to the plant cell, the cells according to the invention can be distinguished from naturally occurring cells, for example, on the basis of the additional expression of nucleic acid molecules according to the invention. For example, the transgenic plant cells contain more or fewer transcripts of the nucleic acid molecules according to the invention. This can be detected by, for example, northern blot analysis. "More" or "fewer" in this context means preferably at least 10% more or fewer, preferably at least 20% more or fewer and especially preferably at least 50% more or fewer transcripts than corresponding untransformed cells. Furthermore, the cells preferably exhibit a corresponding (At least 10%, 20% or 50%, respectively) increase or decrease in the content of protein according to the invention. The transgenic plant cells can be regenerated into intact plants by techniques known to the skilled worker.

The plants obtainable by regenerating the transgenic plant cells according to the invention, and processes for the generation of transgenic plants by regenerating intact plants from the plant cells according to the invention, are also subject matter of the present invention. Another subject matter of the invention are plants which contain the transgenic plant cells according to the invention. In principle, the transgenic plants can be plants of any species, i.e. not only monocotyledonous, but also dicotyledonous plants. The plants are preferably useful plants, i.e. plants which are grown by man for the purposes of nutrition or for technical, in particular industrial, purposes. They are preferably starch-storing plants such as, for example, cereal species (rye, barley, oats, maize, wheat, sorghum and millet, sago etc.), rice, peas, marrowfat peas, cassava, potatoes, tomatoes, oilseed rape, soybeans, hemp, flax, sunflowers, cowpeas, mung beans or arrowroot.

The invention also relates to propagation material of the plants according to the invention, for example fruits, seeds, tubers, root stocks, seedlings, cuttings, calli, protoplasts, cell cultures etc.

Altering the enzymatc activities of the enzymes involved in starch metabolism results in the synthesis, in the plants generated by the process according to the invention, of a starch with a modified structure.

A large number of cloning vectors are available for preparing the introduction of foreign genes into higher plants, vectors which contain a replication signal for *E. coli* and a marker gene for the selection of transformed bacterial cells. Examples of such vectors are pBR322, pUC series, M13mp series, pACYC184 and the like. The desired sequence can be introduced into the vector at a suitable restriction cleavage site. The resulting plasmid is used for transforming *E. coli* cells. Transformed *E. coli* cells are cultured in a suitable medium and then harvested and lysed. The plasmid is recovered. The analytical methods for characterizing the plasmid DNA obtained are generally restriction analyses, gel electrophoreses and other methods of biochemistry and molecular biology (Sambrook et al. loc. cit.). After each manipulation, the plasmid DNA can be cleaved and DNA fragments obtained linked to other DNA sequences. Each plasmid DNA sequence can be cloned into the same or other plasmids.

A large number of techniques are available for introducing DNA into a plant host cell. These techniques encompass the transformation of plant cells with T-DNA using *Agrobacterium tumefaciens* or *Agrobacterium rhizogenes* as the means for transformation, protoplast fusion by means of polyethylene glycol (PEG), injection, DNA electroporation, the introduction of DNA by means of the biolistic method, and other possibilities.

The injection and electroporation of DNA into plant cells requires no particular aspects of the plasmids or the DNA used per se. Simple plasmids such as, for example, pUC derivatives can be used. However, if intact plants are to be regenerated from such transformed cells, the presence of a selectable marker gene is required.

Depending on the method of introducing desired genes into the plant cell, further DNA sequences may be required. If, for example, the Ti or Ri plasmid is used for transforming the plant cell, at least the right border, but frequently the right and left border, of the Ti and Ri plasmid T-DNA must be linked to the genes to be introduced as flanking region. If agrobacteria are used for the transformation, the DNA to be introduced must be cloned into specific plasmids, either into an intermediate vector or into a binary vector. The intermediate vectors can be integrated into the agrobacterial Ti or Ri plasmid by homologous recombination owing to sequences which are homologous to sequences in the T-DNA. The former also contains the vir region required for T-DNA transfer. Intermediate vectors cannot replicate in agrobacteria. The intermediate vector can be transferred to *Agrobacterium tumefaciens* by means of a helper plasmid (conjugation). Binary vectors are capable of replication in *E. coli* and in agrobacteria. They contain a selection marker gene and a linker or polylinker which are framed by the left and right T-DNA border region. They can be transformed directly into the agrobacteria (Holsters et at. (1978) Mol. Gen. Genet. 163: 181–187). The agrobacterium which acts as the host cell should contain a plasmid carrying a vir region. The vir region is required for transferring the T-DNA into the plant cell. Additional T-DNA may be present. The agrobacterium transformed in this way is used for transforming plant cells.

The use of T-DNA for transforming plant cells has been researched intensively and been described in EP 120516; Hoekema, in: The Binary Plant Vector System Offsetdrukkerij Kanters B.V., Alblasserdam (1985), Chapter V; Fraley et al., Crit. Rev. Plant. Sci., 4: 1–46 and An et al. (1985) EMBO J. 4: 277–287.

To transfer the DNA into the plant cell, plant explants can expediently be cocultured with *Agrobacterium tumefaciens* or *Agrobacterium rhizogenes*. Intact plants can then be regenerated from the infected plant material (for example leaf sections, stem segments, roots, but also protoplasts, or plant cells which have been grown in suspension culture) in a suitable medium which can contain antibiotics or biocides for selecting transformed cells. The resulting plants can then be examined for the presence of the DNA which has been introduced. Other possibilities of introducing foreign DNA using the biolistic method or by protoplast transformation are known (cf., for example, Willmitzer, L, 1993 Transgenic plants. In: Biotechnology, A Multi-Volume Comprehensive Treatise (H. J. Rehm, G. Reed, A. Pühler, P. Stadler, eds.), Vol. 2, 627–659, VCH Weinheim-New York-Basle-Cambridge).

While the transformation of dicotyledonous plants via Ti-plasmid vector systems with the aid of *Agrobacterium tumefaciens* is well established, more recent work suggests that even monocotyledonous plants are indeed accessible to transformation by means of agrobacterium-based vectors (Chan et al., Plant Mol. Biol. 22 (1993), 491–506; Hiei et al., Plant J. 6 (1994), 271–282).

Alternative systems for the transformation of monocotyledonous plants are the transformation by means of the biolistic approach, protoplast transformation, the electroporation of partially permeabilized cells, and the introduction of DNA by means of glass fibers.

Specifically, different methods have been described in the literature for the transformation of maize (cf., for example, WO 95/06128, EP 0 513 849; EP 0 465 875). EP 292 435 describes a method with the aid of which fertile plants can be obtained starting from a mucilage-free, friable, granular maize callus. In this context, Shillito et al. (Bio/Technology 7 (1989), 581) have observed that the capacity of regenerating fertile plants requires starting from callus suspension cultures from which a dividing protoplast culture with the capacity of regenerating plants can be made. Following an in-vitro culture period of 7 to 8 months, Shillito et al. obtained plants with viable progeny which, however, have abnormalities with regard to morphology and reproductivity. Prioli and Söndahl (Bio/Technology 7 (1989), 589) also describe the regeneration and obtaining of fertile maize plants from maize protoplasts.

Once the DNA which has been introduced is integrated into the genome of the plant cell, it is, as a rule, stable therein and is also retained in the progeny of the originally transformed cell. It normally contains a selection marker which imparts to the transformed plant cells resistance to a biocide or an antibiotic such as kanamycin, G 418, bleomycin, hygromycin or phosphinotricin and the like. The individual marker chosen should therefore allow selection of transformed cells over cells which lack the DNA which has been introduced.

Within the plant, the transformed cells grow in the customary manner (see also McCormick et al.(1986) Plant Cell Reports 5:81–84). The resulting plants can be grown normally and hybridized with plants which have the same transformed germ plasm or other germ plasm. The resulting hybrids have the corresponding phenotypic features.

Two or more generations should be grown to ensure that the phenotypic feature is stably retained and inherited. Also, seeds should be harvested to ensure that the phenotype in question or other features have been retained.

Yet another subject matter of the invention is a process for the production of starch in a manner known per se, in which plant cells according to the invention, plants according to the invention, plant parts according to the invention or propagation material according to the invention are processed or integrated into the process.

Processes for extracting starch from plants or from starch-storing parts of plants are known to the skilled worker. Processes for extracting starch from maize kernels are described, for example, by Eckhoff et al. (Cereal Chem. 73 (1996) 54–57). As a rule, the extraction of maize starch on the industrial scale is performed by wet milling. Moreover, processes for extracting the starch from various starch-storing plants are described, for example, in "Starch: Chemistry and Technology (eds: Whistler, BeMiller and Paschall (1994), 2nd Edition, Academic Press Inc. London Ltd; ISBN 0-12-746270-8; see, for example, Chapter XII, pages 412–468: maize and sorghum starches: production; by Watson: Chapter XIII, pages 469–479: tapioca, arrowroot and sago starches: production; by Corbishley and Miller; Chapter XIV, pages 479–490: potato starch: production and uses; by Mitch; Chapter XV, pages 491 to 506: wheat starch: production, modification and uses; by Knight and Oson; and Chapter XVI, pages 507 to 528: rice starch: production and uses; by Rohmer and Klem). Devices normally used in processes for extracting starch from plant material are separators, decanters, hydrocyclones, spray dryers and fluidized-bed dryers.

Owing to the expression of a nucleic acid molecule according to the invention, the transgenic plant cells and plants according to the invention synthesize a starch which is modified in comparison to the starch synthesized in wild-type plants for example with regard to its physico-chemical properties.

Yet another subject matter of the invention is the starch which can be obtained from a plant cell according to the invention, plant according to the invention, their propagation material or a method according to the invention.

A further embodiment of the present invention also includes the use of the starch according to the invention in industry for the production of foodstuffs, packaging materials or disposable products.

The starch according to the invention can be modified by processes known to the skilled worker and is suitable, in its unmodified or modified form, for a variety of applications in the food or non-food sector.

In principle, the possible uses of the starch according to the invention can be divided into two important sectors. One sector encompasses the hydrolisates of the starch, mainly glucose and glucose units, which are obtained by enzymatic or chemical methods. They are used as starting material for other chemical modifications and processes such as fermentation. What may be important here is the simplicity and inexpensive design of a hydrolytic process as is currently performed essentially enzymatically using amyloglucosidase. What would be feasible is a financial saving by using less enzyme. This could be caused by altering the structure of the starch, for example increasing the surface area of the granule, by better degradability owing to a lower degree of branching, or by a steric structure which limits the accessibility for the enzymes employed.

The other sector in which starch according to the invention can be used as so-called native starch, due to its polymeric structure, can be divided into two further fields of application:

1. The Food Industry

Starch is a traditional additive to a large number of foodstuffs in which its function is essentially to bind aqueous additives or to cause increased viscosity or else increased gelling. Important characteristics are the visco-elasticity, the sorptive characteristics, the swelling temperature, the gelatinization temperature, the viscosity and thickening power, starch solubility, transparency and gel structure, thermal stability, shear stability, stability to acids, the tendency to undergo retrogradation, the film-forming capacity, the freeze-thaw stability, digestibility and the ability of forming complexes with, for example, inorganic or organic ions.

2. The Non-food Industry

In this important sector, starch is employed as an auxiliary for various preparation processes or as an additive in industrial products. When using starch as an auxiliary, mention must be made, in particular, of the paper and board industry. Starch acts mainly for retardation purposes (retaining solids), binding filler particles and fines, as a stiffener and for dehydration. Moreover, the advantageous properties of starch regarding stiffness, strength, sound, touch, luster, smoothness, bonding strength and the surfaces are made use of.

2.1. The Paper and Board Industry

Within the papermaking process, four fields of application must be distinguished, i.e. surface, coating, stock and spraying. With 80% of the consumption, surface starch accounts for by far the greatest starch quantity, 8% are used as coating starch, 7% as stock starch and 5% as spraying starch.

The demands on starch with regard to surface treatment are essentially high whiteness, an adapted viscosity, highly stable viscosity, good film formation and low dust formation. When used for coating, the solids content, an adapted viscosity, a high binding capacity and a high pigment affinity play an important role. Of importance when used as an additive to the stock is rapid, uniform, loss-free distribution, high mechanical strength and complete retention in the paper web. If the starch is used in the spraying sector, again, an adapted solids content, high viscosity and a high binding capacity are of importance.

2.2. The Adhesives Industry

An important field of application for starches is in the adhesives industry, where the potential uses can be divided into four subsections: the use as a pure starch paste, the use in starch pastes which have been treated with specialty chemicals, the use of starch as additive to synthetic resins and polymer dispersions, and the use of starches as extenders for synthetic adhesives. 90% of the starch based adhesives is employed in the sectors production of corrugated board, production of paper sacks and bags, production of composite materials for paper and aluminum, production of box board and gumming adhesives for envelopes, stamps and the like.

2.3. The Textiles and Textile Care Products Industry

An important field of application for starches as auxiliaries and additive is the sector production of textiles and textile care products. The following four fields of application must be distinguished within the textiles industry: the use of starch as sizing agent, i.e. as auxiliary for smoothing and strengthening the burring behavior as a protection from the tensile forces applied during weaving, and for increasing resistance to abrasion during weaving, starch as a textile finishing agent, in particular after quality-reducing pretreatments such as bleaching, dyeing and the like, starch as thickener in the preparation of dye pastes for preventing bleeding, and starch as additive to chaining agents for sewing threads.

2.4. The Construction Materials Industry

The fourth field of application is the use of starches as additive in construction materials. An example is the production of gypsum plasterboards, where the starch which is admixed to the gypsum slurry gelatinizes with the water, diffuses to the surface of the plaster core, where it binds the boards to the core. Other fields of application are the admixture to rendering and mineral fibers. In the case of ready-mixed concrete, starch products are employed for delaying binding.

2.5. Soil Stabilization

A limited market for starch products is the production of soil stabilizers, which are employed for the temporary protection of the soil particles from water when the soil is disturbed artificially. According to present knowledge, product combinations of starch and polymer emulsions equal the previously employed products with regard to their erosion- and crust-reducing effect, but are markedly less expensive.

2.6. Use in Crop Protection Products and Fertilizers

One field of application for using starch is in crop protection products for altering the specific properties of the products. Thus, starches are employed for improving the wettability of crop protection products and fertilizers, for the controlled release of the active ingredients, for converting liquid active ingredients, volatile active ingredients and/or active ingredients with an offensive odor into microcrystalline, stable, shapeable substances, for mixing incompatible compounds, and for extending the duration of action by reducing decomposition.

2.7. Pharmaceuticals, Medicine, and the Cosmetics Industry

Another field of application is the sector of pharmaceuticals, medicine and the cosmetics industry. In the pharmaceuticals industry, starches are employed as binders for tablets or for diluting the binder in capsules. Moreover, starches are used as tablet disintegrants, since they absorb fluids after swallowing and swell within a short time to such an extent that the active ingredient is liberated. Medicinal lubricating powders and wound powders are starch-based for reasons of quality. In the cosmetics sector, starches are employed, for example, as carriers of powder additives such as fragrances and salicylic acid. A relatively large field of application for starch is toothpaste.

2.8. Addition of Starch to Coal and Briquettes

A field of application for starch is as additive to coal and briquettes. With an addition of starch, coal can be agglomerated, or briquetted, in terms of high quantity, thus preventing early decomposition of the briquettes. In the case of barbecue coal, the starch addition amounts to between 4 and 6%, in the case of calorized coal to between 0.1 and 0.5%. Moreover, starches are gaining importance as binders since the emission of noxious substances can be markedly reduced when starches are added to coal and briquettes.

2.9. Ore Slick and Coal Silt Processing

Furthermore, starch can be employed as flocculant in ore slick and coal silt processing.

2.10. Foundry Auxiliary

A further field of application is as additive to foundry auxiliaries. Various casting processes require cores made with sands treated with binders. The binder which is predominantly employed nowadays is bentonite, which is treated with modified starches, in most cases swellable starches.

The purpose of adding starch is to increase flowability and to improve the binding power. In addition, the swellable starches can meet the demands of production engineering, such as being cold-water dispersible, rehydratable and readily miscible with sand and having high water binding capacity.

2.11. Use in the Rubber Industry

In the rubber industry, starch is employed for improving the technical and visual quality. The reasons are the improvement of the surface luster, the improvement of handle and of appearance, and to this end starch is scattered over the tacky gummed surfaces of rubber materials prior to cold curing, and also the improvement of the rubber's printability.

2.12. Production of Leather Substitutes

Modified starches may furthermore also be sold for the production of leather substitutes.

2.13. Starch in Synthetic Polymers

In the polymer sector, the following fields of application can be envisaged: the incorporation of starch degradation products in the processing process (starch is only a filler, there is no direct bond between the synthetic polymer and the starch) or, alternatively, the incorporation of starch degradation products in the production of polymers (starch and polymer form a stable bond).

The use of starch as pure filler is not competitive in comparison with other substances such as talc. However, this is different when the specific properties of starch make an impact and thus markedly alter the spectrum of characteristics of the end products. An example of this is the use of starch products in the processing of thermoplasts, such as polyethylene. Here, the starch and the synthetic polymer are combined by coexpression in the ratio 1:1 to give a master batch, from which various products are produced together with granulated polyethylene, using conventional process techniques. By incorporating starch in polyethylene films, an increased substance permeability in the case of hollow bodies, an improved permeability for water vapor, an improved antistatic behavior, an improved antiblock behavior and an improved printability with aqueous inks can be achieved. The current disadvantages relate to the insufficient transparency, the reduced tensile strength, and a reduced elasticity.

Another possibility is the use of starch in polyurethane foams. By adapting the starch derivatives and by processing-engineering optimization, it is possible to control the reaction between synthetic polymers and the starches' hydroxyl groups in a direct manner. This results in polyurethane films which have the following spectrum of properties, owing to the use of starch: a reduced heat extension coefficient, a reduced shrinking behavior, an improved pressure-tension behavior, an increase in permeability for water vapor without altering the uptake of water, a reduced flammability and a reduced ultimate tensile strength, no drop formation of combustible parts, freedom from halogens, and reduced aging. Disadvantages which still exist are a reduced printability and a reduced impact strength. Product development is currently no longer restricted to films. Solid polymer products such as pots, slabs and dishes with a starch content of over 50% may also be produced. Moreover, starch/polymer mixtures are considered advantageous since their biodegradability is much higher.

Starch graft polymers have become exceedingly important owing to their extremely high water binding capacity. They are products with a starch backbone and a side chain of a synthetic monomer, grafted on using the principle of the free-radical chain mechanism. The starch graft polymers which are currently available are distinguished by a better binding and retention capacity of up to 1000 g water per g of starch, combined with high viscosity. The fields of application for these superabsorbers have extended greatly in recent years and are, in the hygiene sector, the products diapers and pads, and, in the agricultural sector, for example in seed coatings.

What is decisive for the application of novel, genetically modified starches are, on the one hand, structure, water content, protein content, lipid content, fiber content, ash/phosphate content, amylose/amylopectin ratio, molecular mass distribution, the degree of branching, granule size, granule shape and crystallization, and, on the other hand, also the characteristics which affect the following features: viscoelasticity, sorption characteristics, gelatinization temperature, viscosity, thickening powder, solubility, gel structure, transparency, thermal stability, shear stability, stability to acids, tendency to undergo retrogradation, gel formation, freeze-thaw stability, complex formation, iodine binding, film formation, adhesive power, enzyme stability, digestibility and reactivity.

The production of modified starches by recombinant methods can, on the one hand, alter the properties, for example of the starch derived from the plant, in such a way that other modifications by means of chemical or physical alterations are no longer required. On the other hand, starches which have been modified by recombinant methods may be subjected to further chemical modifications, which leads to further improvements in quality for some of the above-described fields of application. These chemical modifications are known in principle. They are, in particular, modifications by thermal and pressure treatment, treatment with organic or inorganic acids, enzymatic treatment, oxidations or esterifications, which lead, for example, to the formation of phosphate starches, nitrate starches, sulfate starches, xanthate starches, acetate starches and citrate starches. Moreover, mono- or polyhydric alcohols in the presence of strong acids may be employed for producing starch ethers, resulting in starch alkyl-ethers, O-allyl ethers, hydroxyalkyl ethers, O-carboxy/methyl ethers, N-containing starch ethers, P-containing starch ethers, S-containing starch ethers, crosslinked starches or starch graft polymers.

A use of the starches according to the invention is in industrial application, preferably for foodstuffs or the production of packaging materials and dispersible articles.

The examples which follow serve to illustrate the invention and constitute in no way a restriction.

Abbreviations used:

| | |
|---|---|
| BE | branching enzyme |
| bp | base pair |
| IPTG | isopropyl β-D-thiogalactopyranoside |
| SS | soluble starch synthase |
| PMSF | phenylmethylsulfonyl fluoride |

Media and solutions used in the examples:

| | |
|---|---|
| 20 × SSC | 175.3 g NaCl |
| | 88.2 g sodium citrate |
| | to 1000 ml with twice-distilled H$_2$O |
| | pH 7.0 with 10N NaOH |
| Buffer A | 50 mM Tris-HCl pH 8.0 |
| | 2.5 mM DTT |
| | 2 mM EDTA |
| | 0.4 mM PMSF |
| | 10% glycerol |
| | 0.1% sodium dithionite |
| Buffer B | 50 mM Tris-HCl pH 7.6 |
| | 2.5 mM DTT |
| | 2 mM EDTA |
| Buffer C | 0.5M sodium citrate pH 7.6 |
| | 50 mM Tris-HCl pH 7.6 |
| | 2.5 mM DTT |
| | 2 mM EDTA |
| 10 × TBS | 0.2M Tris-HCl pH 7.5 |
| | 5.0M NaCl |
| 10 × TBST | 10 × TBS |
| | 0.1% (v/v) Tween 20 |
| Elution buffer | 25 mM Tris pH 8.3 |
| | 250 mM glycine |
| Dialysis buffer | 50 mM Tris-HCl pH 7.0 |
| | 50 mM NaCl |
| | 2 mM EDTA |
| | 14.7 mM β-mercaptoethanol |
| | 0.5 mM PMSF |
| Protein buffer | 50 mM sodium phosphate buffer pH 7.2 |
| | 10 mM EDTA |
| | 0.5 mM PMSF |
| | 14.7 mM β-mercaptoethanol |

DESCRIPTION OF THE FIGURES

FIG. 1 represents a schematic RVA temperature profile (viscosity vs. time [min]) with the viscosimetric parameters T=gelatinization temperature, temperature at the point in time when gelatinization starts; Max specifies the maximum viscosity; Min specifies the minimum viscosity; Fin specifies the viscosity at the end of the measurement; Set is the difference (Δ) of Min and Fin (setback).

The following methods were used in the examples
1. Cloning Method

The vector pBluescript II SK (Stratagene) was used for cloning into E. coli.

For the transformation of plants, the gene constructs were cloned into the binary vector pBinAR Hyg (Höfgen & Willmitzer, 1990, Plant Sci. 66:221–230) and pBinB33-Hyg.

2. Bacterial Strains and Plasmids

The E. coli strain DH5α (Bethesda Research Laboratories, Gaithersburgh, USA) was used for the Bluescript vector p Bluescript II KS (Stratagene) and for the pBinAR Hyg and pBinB33 Hyg constructs. The E. coli strain XL1-Blue was used for the in vivo exclusion.

pBinAR

The plasmid pBinAR is a derivative of the binary vector plasmid pBin19 (Bevan, 1984, Nucl. Acid Res. 12:8711–8721), which was constructed as follows: a 529 bp fragment encompassing the nucleotides 6909–7437 of the cauliflower mosaic virus promoter 35S promoter was isolated from plasmid pDH51 as EcoRI/KpnI fragment (Pietrzak et al., 1986), ligated between the EcoRI and KpnI cleavage sites of the pUC18 polylinker, and was termed plasmid pUC18-35S. With the aid of the restriction endonucleases HindIII and PvuII, a 192 bp fragment was isolated from plasmid pAGV40 (Herrera-Estrella et al., 1983), which encompasses DNA of the Ti-plasmid pTiACH5 (Gielen et al, 1984, EMBO J.:835–846) (nucleotides 11749–11939). After the PvuII cleavage sites had been provided with SphI linkers, the fragment was ligated between the SpHI and HindIII cleavage sites of pUC18-35S, and this was termed plasmid pA7. Moreover, the entire polylinker comprising the 35S promoter and the ocs terminator was excised with EcoRI and HindIII and ligated into the appropriately cleaved pBin19. This gave rise to the plant expression vector pBinAR (Höfgen and Willmitzer, 1990).

pBinB33

The promoter of the Solanum tuberosum patatin gene B33 (Rocha-Sosa et al., 1989) was ligated, as DraI fragment (nucleotides –1512–+14) into the vector pUC19, which had been cleaved with Sst I and which had been made blunt-ended with the aid of T4-DNA polymerase. This gave rise to plasmid pUC19-B33. The B33 promoter was excised from this plasmid with EcoRI and SmaI and ligated into the appropriately cleaved vector pBinAR. This gave rise to the plant expression vector pBinB33.

pBinAR-Hyg

Starting from plasmid pA7 (cf. description of vector pBinAR), the EcoRI-HindIII fragment comprising the 35S promoter, the ocs terminator and the portion of the polylinker situated between the 35S promoter and the ocs terminator was introduced into the appropriately cleaved plasmid pBin-Hyg.

pBinB33-Hyg

Starting from plasmid pBinB33, the EcoRI-HindIII fragment comprising the B33 promoter, part of the polylinker and the ocs terminator was excised and ligated into the appropriate cleaved vector pBin-Hyg. This gave rise to the plant expression vector pBinB33-Hyg.

3. Transformation of Agrobacterium tumefaciens

The DNA was transferred by direct transformation using the method of Höfgen&Willmitzer (1988, Nucleic Acids Res. 16:9877). The plasmid DNA of transformed agrobacteria was isolated using the method of Bimboim&Doly (1979, Nucleic Acids Res. 7:1513–1523), subjected to suitable restriction cleavage, and then analyzed by gel electrophoresis.

4. Transformation of Potatoes

The transformation of the plasmids into the potato plants (Solanum tuberosum L.cv. Desiree, Vereinigte Saatzuchten eG, Ebstorf) was carried out with the aid of the Agrobacterium tumefaciens strain C58C1 (Dietze et al. (1995) in Gene Transfer to Plants. pp. 24–29, eds.: Potrykus, I. and Spangenberg, G., Springer Verlag, Deblaere et al., 1985, Nucl. Acids Res. 13:4777–4788).

Ten small leaves of a sterile potato culture which had been scarified with a scalpel were placed into 10 ml of MS medium (Murashige&Skoog (1962) Physiol. Plant. 15: 473) supplemented with 2% sucrose and containing 50 ml of an *Agrobacterium tumefaciens* overnight culture grown under selection conditions. After the culture had been shaken gently for 3–5 minutes, it was incubated for 2 more days in the dark. For callus induction, the leaves were then placed on MS medium supplemented with 1.6% glucose, 5 mg/l naphthylacetic acid, 0.2 mg/l benzylaminopurin, 250 mg/l claforan, 50 mg/l kanamycin, and 0.80% Bacto agar. After the leaves had been incubated for one week at 25° C. and 3000 Lux, they were placed on MS medium supplemented with 1.6% glucose, 1.4 mg/l zeatin ribose, 20 mg/l naphthylacetic acid, 20 mg/l gibberellic acid, 250 mg/l claforan, 50 mg/l kanamycin and 0.80% Bacto agar, to induce shoots.

5. Plant Culture Regime

Potato plants were kept in the greenhouse under the following conditions:

| light period | 16 h at 25,000 Lux and 22° C. |
| --- | --- |
| dark period | 8 h at 15° C. |
| atmospheric humidity | 60% |

6. Radiolabeling of DNA Fragments

The DNA fragments were radiolabeled with the aid of a DNA Random Primer Labeling Kit by Boehringer Mannheim (Germany) following the manufacturers instructions.

7. Determination of Starch Synthase Activity

Determination of starch synthase activity was done by determining the incorporation of $^{14}C$ glucose from ADP[$^{14}C$ glucose] into a product which is insoluble in methanol/KCl, as described by Denyer & Smith, 1992, Planta 186:609–617.

8. Detection of Soluble Starch Synthases in the Native Gel

To detect the activity of soluble starch syntheses by non-denaturing gel electrophoresis, tissue samples of potato tubers were hydrolyzed in 50 mM Tris-HCl pH 7.6, 2 mM DTT, 2.5 mM EDTA, 10% glycerol and 0.4 mM PMSF. The electrophoresis was carried out in a MiniProtean II chamber (BioRAD). The monomer concentration of the gels, which had a thickness of 1.5 mm, was 7.5% (w/v), and 25 mM Tris-glycine pH 8.4 was used as gel buffer and running buffer. Identical amounts of protein extract were applied and separated for 2 hours at 10 mA per gel.

The activity gels were subsequently incubated in 50 mM Tricine-NaOH pH 8.5, 25 mM potassium acetate, 2 mM EDTA, 2 mM DTT, 1 mM ADP-glucose, 0.1% (w/v) amylopectin and 0.5 M sodium citrate. The glucans formed were stained with Lugol's solution.

9. Starch Analysis

The starch formed by the transgenic potato plants was characterized by the following methods:

a) Determination of the Amylose/amylopectin Ratio in Starch from Potato Plants

Starch was isolated from potato plants by standard methods, and the amylose:amylopectin ratio was determined by the method described by Hovenkamp-Hermelink et al. (Potato Research 31 (1988) 241–246).

b) Determination of the Phosphate Content

In potato starch, some glucose units may be phosphorylated on the carbon atoms of position C2, C3 and C6. To determine the degree of phosphorylation at position C6 of the glucose, 100 mg of starch were hydrolyzed for 4 hours at 95° C. in 1 ml of 0.7 M HCl (Nielsen et al. (1994) Plant Physiol. 105: 111–117). Following neutralization with 0.7 M KOH, 50 ml of the hydrolysate were subjected to a visual-enzymatic test to determine glucose-6-phosphate. The change in absorption of the test batch (100 mM imidazole/HCl; 10 mM $MgCl_2$; 0.4 mM NAD; 2 units *Leuconostoc mesteroides* glucose-6-phosphate dehydrogenase; 30° C.) was monitored at 334 nm.

The total phosphate was determined as described by Ames, 1996, Methods in Enzymology VIII, 115–118.

c) Analysis of the Amylopectin Side Chains

To analyze distribution and length of the side chains in the starch samples, 1 ml of a 0.1% starch solution was digested with 0.4 U of isoamylase (Megazyme International Ireland Ltd., Bray, Ireland) overnight at 37° C. in 100 mM sodium citrate buffer, pH 3.5.

The rest of the analysis was carried out as described by von Tomlinson et al., (1997), Plant J. 11:31–47, unless otherwise specified.

d) Granule Size Determination

The granule size was determined using a "Lumosed" photosedimentometer by Retsch GmbH, Germany. To this end, 0.2 g of starch was suspended in approx. 150 ml of water and immediately measured. The program supplied by the manufacturer calculated the mean diameter of the starch granules, assuming an average starch density of 1.5 g/l.

e) Gelatinization Properties

The gelatinization or viscosity properties of the starch were recorded using a Viscograph E by Brabender OHG, Germany, or a Rapid Visco Analyser, Newport Scientific Pty Ltd., Investment Support Group, Warriewood NSW 2102, Australia. When using the Viscograph E, a suspension of 30 g of starch in 450 ml of water was subjected to the following heating program: heat from 50° C. to 96° C. at 3°/min, hold for 30 minutes, cool to 30° C. at 3°/min and hold again for 30 minutes. The temperature profile gave characteristic gelatinization properties.

When measuring using the Rapid Visco Analysers (RVA) a suspension of 2 g of starch in 25 ml of water was subjected to the following heating program: suspend for 60 seconds at 50° C., heat from 50° C. to 95° C. at 12°/min, hold for 2.5 minutes, cool to 50° C. at 12° C./min and hold again for 2 minutes. The RVA temperature profile gave the viscosimetric parameters of the tested starches for the maximum viscosity (Max), the end viscosity (Fin), the gelatinization temperature (T), the minimum viscosity (Min) occurring after the maximum viscosity and the difference between minimum viscosity and end viscosity (Setback, Set) (cf. Table 1 and FIG. 1).

f) Determination of the Gel Strength

To determine the gel strength by means of a Texture Analyser, 2 g of starch were gelatinized in 25 ml of water (cf. RVA measurement) and then stored for 24 hours in a sealed container at 25° C. with the exclusion of air. The samples were mounted underneath the probe (circular stamp) of a TA-XT2 Texture Analyser (Stable Micro Systems), and the gel strength was determined with the following parameter settings:

| Test speed | 0.5 mm |
| --- | --- |
| Penetration depth | 7 mm |
| Contact area (of the stamp) | 113 $mm^2$ |
| Pressure/contact area | 2 g |

10. Determination of Glucose, Fructose and Sucrose

To determine the glucose, fructose and sucrose content, small tuber portions (diameter approx. 10 mm) of potato tubers were frozen in liquid nitrogen and then extracted for 30 minutes at 80° C. in 0.5 ml of 10 mM HEPES, pH 7.5; 80% (vol/vol) ethanol. The supernatant, which contains the solubles, was removed and the volume was determined. The supernatant was used for determining the amount of soluble sugars. The quantitative determination of soluble glucose, fructose and sucrose was carried out in a batch of the following composition 100.0 mM imidazole/HCl, pH 6.9
1.5 mM MgCl$_2$
0.5 mM NADP$^+$
1.3 mM ATP
10–50 µl sample
1.0 U yeast glucose-6-phosphate dehydrogenase The batch was incubated for 5 minutes at room temperature. The sugars were subsequently determined photometrically by measuring the absorption at 340 nm after the successive addition of 1.0 unit yeast hexokinase (to determine glucose), 1.0 unit yeast phosphoglucoisomerase (to determine fructose), and 1.0 unit yeast invertase (to determine sucrose).

USE EXAMPLES

Example 1

Isolation of a cDNA Fragment Encoding Potato α-glucosidase

Total RNA of potato tuber tissue directly underneath (approx. 1 cm) germinating shoots were prepared by standard methods (Sambrook et al., 1989).

The purified total RNA was used as starting material for the preparation of poly A+ RNA (Oligotex, mRNA Purification Kit, in accordance with the manufacturer's instructions). 5 µg of this poly A+ RNA were used to generate a cDNA library (λ ZAPII, Stratagene).

Approximately 3×10$^5$ plaque-forming units (pfus) of this unamplified cDNA library (primary library) were plated following the manufacturer's instructions (Stratagene) for plaque lifting. The radiolabeled probe (Random Primed DNA Labeling Kit, following the manufacturer's instructions) used for plaque hybridization was the sequence of Genbank Accession No. T76451. The filters were prehybridized for 4 hours at 42° C. (buffer: 5×SSC, 0.5% BSA, 5×Denhardt, 1% SDS, 40 mM phosphate buffer, pH 7.2, 100 mg/l herring sperm DNA, 25% formamide) and subsequently hybridized for 14 hours at the same temperature. After hybridization, the filters were washed 3× for 20 minutes with 3×SSC, 0.5% SDS at 42° C. and autoradiographed. Hybridizing plaques were singled out, and the phages isolated were used for in-vivo excision following the manufacturer's instructions. Plasmid DNA from the bacterial colonies obtained were isolated, employed for sequence analysis and identified as SEQ ID NO: 1.

A plasmid DNA isolated in this manner was deposited on Jul. 24, 1998 at the Deutsche Sammlung für Mikroorganismen und Zellkulturen (DSMZ) Brunswick, FRG, under the number DSM 12347.

Example 2

Preparation of Plasmid p35SαSSI-Hyg

A 1831 bp Asp718/XbaI fragment containing a partial cDNA encoding the potato SSS I (Abel, G., (1995) PhD Thesis, Free University of Berlin), was inserted between the Asp 718 and XbaI cleavage site of the vector pBinAR-Hyg in antisense orientation relative to the 35S promoter.

Example 3

Preparation of Plasmid p35S-SSI-Kan

A 2384 bp EcoRI fragment containing a cDNA encoding potato SSI (Abel 1995, loc. cit.) was made blunt-ended and introduced into the vector pBinAR, which had previously been cut with SmaI, in sense orientation relative to the 35S promoter.

Example 4

Preparation of Plasmid p35SαSSII-Kan

A 1959 bp SmaI/Asp718 fragment containing a partial cDNA encoding the potato SS II (Abel, 1995, termed GBSS II therein) was made blunt-ended and introduced into the SmaI cleavage site of the vector pBinAR in anti-sense orientation relative to the 35S promoter.

Example 5

Preparation of Plasmid pB33-SSII-Hyg

A 2619 bp SmaI/SalI fragment containing a cDNA encoding the potato SS II (Abel, 1995, loc. cit.) was introduced into the vector pBinB33-Hyg, which had previously been cut with SmaI and SalI in sense orientation relative to the B33 promoter.

Example 6

Preparation of Plasmid p35SαSSIII-Hyg

A 4212 bp Asp718/XbaI fragment containing a cDNA encoding the potato SS III (Abel et al 1996, Plant J. 10(6):981–991), was inserted between the Asp718 and the XbaI cleavage site of the vector pBinAR-Hyg in antisense orientation relative to the 35S promoter.

Example 7

Preparation of Plasmid p35S-SSIII-Kan

A 4191 bp EcoRI fragment containing a cDNA encoding potato SS III (Abel et al., 1996, loc. cit.), was made blunt-ended and introduced into the SmaI cleavage site of the vector pBinAR in sense orientation relative to the 35S promoter.

Example 8

Preparation of Plasmid pB33αBEαSSIII-Kan

A 1650 bp HindII fragment which contains a partial cDNA encoding the potato BE enzyme (Kossmann et al., 1991, Mol. & Gen. Genetics 230(1–2):3944) was made blunt-ended and introduced in antisense orientation relative to the B33 promoter into the vector pBinB33 which had been precut with SmaI. The resulting plasmid was cut open with BamHI. A 1362 Bp BamHI fragment containing a partial cDNA encoding the potato SS III enzyme (Abel et al., 1996, loc. cit.) was introduced into the cleavage site, again in antisense orientation relative to the B33 promoter.

Example 9

Preparation of Plasmid p35SαSSII-αSSIII-Kan

A 1546 bp EcoRV/HincII fragment containing a partial cDNA encoding the potato SS II (Abel, 1995, loc. cit.) was cloned into the vector pBluescript II KS which can been cut with EcoRV/HincII, then excised again by digestion with Asp718/BamHI and introduced in antisense orientation relative to the 35S promoter into the vector pBinAR which had been digested in the same manner. Then, a 1356 bp BamHI fragment containing a partial cDNA encoding the potato SS III (Abel et al., 1996, loc. cit.), was introduced into the BamHI cleavage site of the vector pBinAR-αSSII, again in antisense orientation.

Example 10

Preparation of Plasmid pB33αSSIαSSIαSSIII-Kan

A 2384 bp EcoRI fragment containing a cDNA encoding the potato SS I (Abel, 1995, loc. cit.) was made blunt-ended and cloned into the SmaI cleavage site of the pBinB33 vector in antisense orientation relative to the B33 promoter. A 1362 bp BamHI fragment containing a partial cDNA encoding the potato SS III (Abel et al., 1996, loc. cit.) was introduced into the BamHI cleavage site of the resulting vector, again in antisense orientation relative to the B33 promoter.

Example 11

Preparation of Plasmid p35SαSSII-Hyg

A 1959 bp SmaI/Asp718 fragment containing a partial cDNA encoding the SS II (Abel, 1995, loc. cit.), was made blunt-ended and introduced into the SmaI cleavage site of the pBinAR-Hyg vector in antisense orientation relative to the 355 promoter.

Example 12

Introduction of the Plasmids into the Genome of Potato Cells

The plasmids stated in Examples 1 to 11 were transferred, either individually and/or in succession, into agrobacteria, with the aid of which potato cells were transformed as described above. Subsequently, intact plants were regenerated from the transformed plant cells.

Example 13

Characterization of the Physicochemical Properties of the Modified Starches

As a result of the transformation, the transgenic potato plants showed a change in the physico-chemical properties of the starches synthesized by them. The starch formed by these plants differs for example from starch synthesized in wild-type plants with regard to its phosphate or amylose content, the viscosity or gelatinization properties determined by RVA, and its chromotographic behavior.

I claim:

1. An isolated nucleic acid molecule encoding a protein with the function of a potato α-glucosidase, selected from the group consisting of
   a) nucleic acid molecules which encode a protein which comprises the amino acid sequence stated under SEQ ID NO: 2,
   b) nucleic acid molecules which comprise the nucleotide sequence shown under SEQ ID NO: 1;
   c) nucleic acid molecules which have over 85% sequence identity to the nucleotide sequence shown under SEQ ID NO:1, and
   d) nucleic acid molecules whose nucleotide sequence deviates from the sequence of the nucleic acid molecules stated under b) owing to the degeneracy of the genetic code.

2. The nucleic acid molecule as claimed in claim 1, which is a deoxyribonucleic acid molecule.

3. The nucleic acid molecule as claimed in claim 1, which is a cDNA molecule.

4. The nucleic acid molecule as claimed in claim 1, which is a ribonucleic acid molecule.

5. An isolated nucleic acid molecule which specifically hybridizes with the nucleic acid molecule as claimed in claim 1, under highly stringent conditions followed by a wash step, wherein hybridization temperature is at 68° C. and is followed by a wash at 68° C. in a wash buffer containing 0.2×SSC.

6. A vector comprising the nucleic acid molecule as claimed in claim 1.

7. A vector comprising the nucleic acid molecule as claimed in claim 1, wherein the nucleotide sequence encoding a protein with the function of an α-glucosidase or parts thereof is present in sense or antisense orientation.

8. A vector comprising the nucleic acid molecule as claimed in claim 1, which is linked to regulatory elements that initiate transcription of RNA in a cell.

9. A host cell which is transformed with the nucleic acid molecule as claimed in claim 1, or with a the vector as claimed in claim 6; or a cell which is derived from the host cell, and which comprises said nucleic acid molecule or vector.

10. A method for making a transgenic plant cell which synthesizes a modified starch, wherein the nucleic acid molecule as claimed in claim 1, or the vector as claimed in claim 6, is integrated into the genome of a plant cell.

11. A plant cell which is made by the method of claim 10.

12. A transgenic plant comprising the nucleic acid molecule of claim 1.

13. A transgenic plant comprising the plant cell of claim 11.

* * * * *